(12) United States Patent
Yavorsky

(10) Patent No.: US 9,033,924 B2
(45) Date of Patent: May 19, 2015

(54) SYSTEMS FOR FLUID RESERVOIR RETENTION

(71) Applicant: MEDTRONIC MINIMED, INC., Northridge, CA (US)

(72) Inventor: Matthew William Yavorsky, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 213 days.

(21) Appl. No.: 13/745,650

(22) Filed: Jan. 18, 2013

(65) Prior Publication Data
US 2014/0207066 A1 Jul. 24, 2014

(51) Int. Cl.
*A61M 5/14* (2006.01)

(52) U.S. Cl.
CPC .................. *A61M 5/1413* (2013.01)

(58) Field of Classification Search
CPC ............... A61M 5/14; A61M 5/1413; A61M 2005/14573; A61M 2005/2492
USPC .................. 604/533, 326, 175, 151
See application file for complete search history.

(56) References Cited

U.S. PATENT DOCUMENTS

| | | | |
|---|---|---|---|
| 3,631,847 A | 1/1972 | Hobbs, II | |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Quynh-Nhu H Vu
(74) *Attorney, Agent, or Firm* — Ingrassia Fisher & Lorenz, P.C.

(57) ABSTRACT

A fluid reservoir for use with a fluid infusion device is provided. The fluid reservoir can include a first portion having a first end and a second end. The first end can include an alignment feature and a delivery port. The fluid reservoir can include a second portion coupled to the second end of the first portion, with a portion of the second portion movable within the first portion to advance a fluid out of the delivery port. The fluid reservoir can also include a reservoir defined between the first portion and the second portion that receives the fluid.

15 Claims, 20 Drawing Sheets

(56) References Cited

U.S. PATENT DOCUMENTS

| | | | |
|---|---|---|---|
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 4,936,833 A * | 6/1990 | Sams | 604/232 |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,611,785 A * | 3/1997 | Mito et al. | 604/239 |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |

(56) References Cited

U.S. PATENT DOCUMENTS

| | | | |
|---|---|---|---|
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,828,764 B2 | 11/2010 | Moberg et al. | |
| 7,905,868 B2 | 3/2011 | Moberg et al. | |
| 8,512,287 B2 | 8/2013 | Cindrich et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0161744 A1* | 8/2003 | Vilks et al. | 417/415 |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0204673 A1 | 10/2004 | Flaherty | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0078393 A1* | 4/2007 | Lynch et al. | 604/131 |
| 2007/0088521 A1 | 4/2007 | Shmueli et al. | |
| 2007/0135866 A1 | 6/2007 | Baker et al. | |
| 2008/0077081 A1* | 3/2008 | Mounce et al. | 604/67 |
| 2008/0154503 A1 | 6/2008 | Wittenber et al. | |
| 2008/0269687 A1 | 10/2008 | Chong et al. | |
| 2009/0081951 A1 | 3/2009 | Erdmann et al. | |
| 2009/0082635 A1 | 3/2009 | Baldus et al. | |
| 2009/0299290 A1 | 12/2009 | Moberg | |
| 2010/0137790 A1* | 6/2010 | Yodfat | 604/67 |
| 2010/0325864 A1* | 12/2010 | Briones et al. | 29/428 |
| 2011/0160654 A1 | 6/2011 | Hanson et al. | |
| 2011/0160655 A1 | 6/2011 | Hanson et al. | |
| 2011/0160666 A1 | 6/2011 | Hanson et al. | |
| 2011/0160667 A1* | 6/2011 | Bazargan et al. | 604/151 |
| 2012/0215179 A1 | 8/2012 | Halili et al. | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.

(56) References Cited

OTHER PUBLICATIONS (MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

(56) References Cited

OTHER PUBLICATIONS

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series Vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

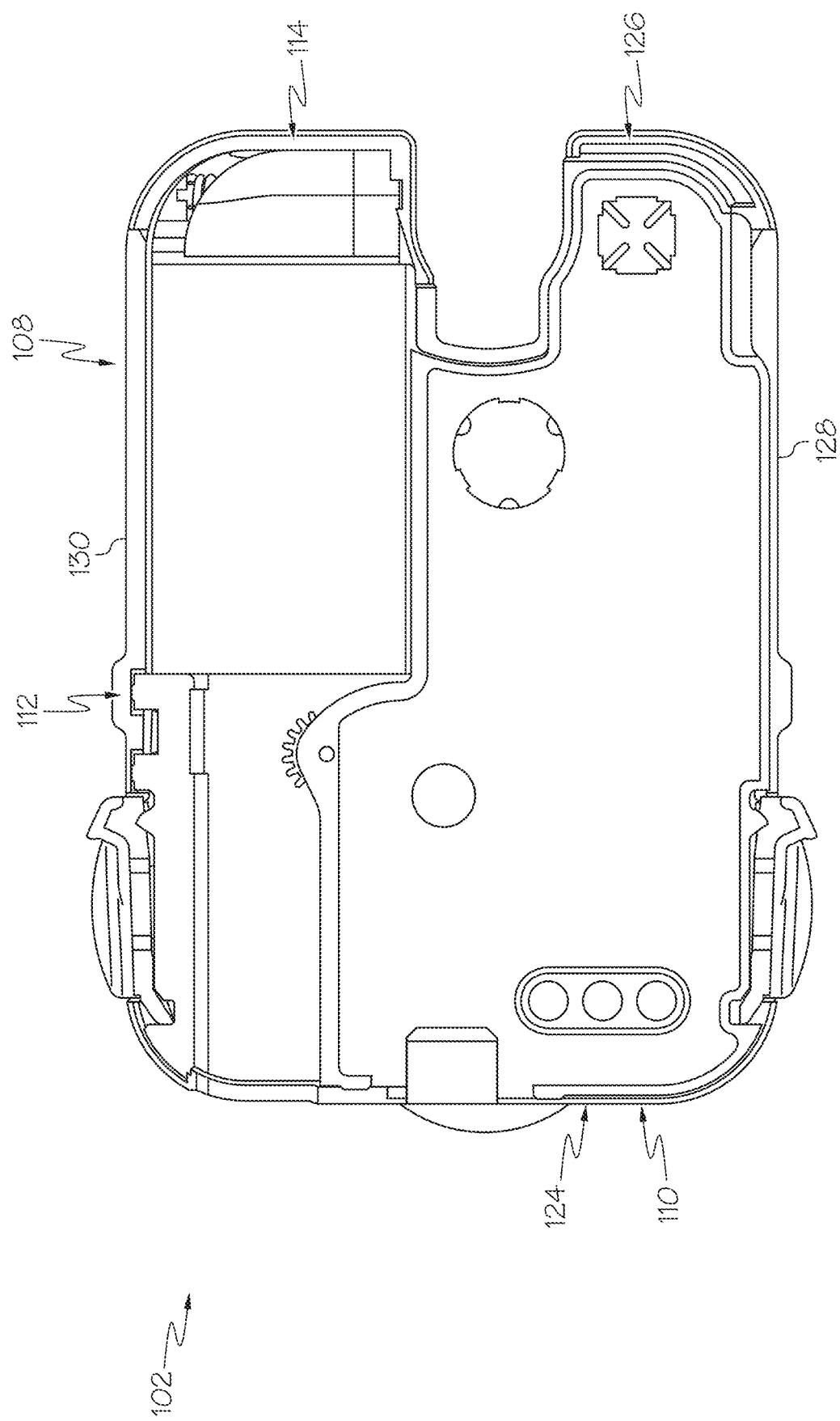

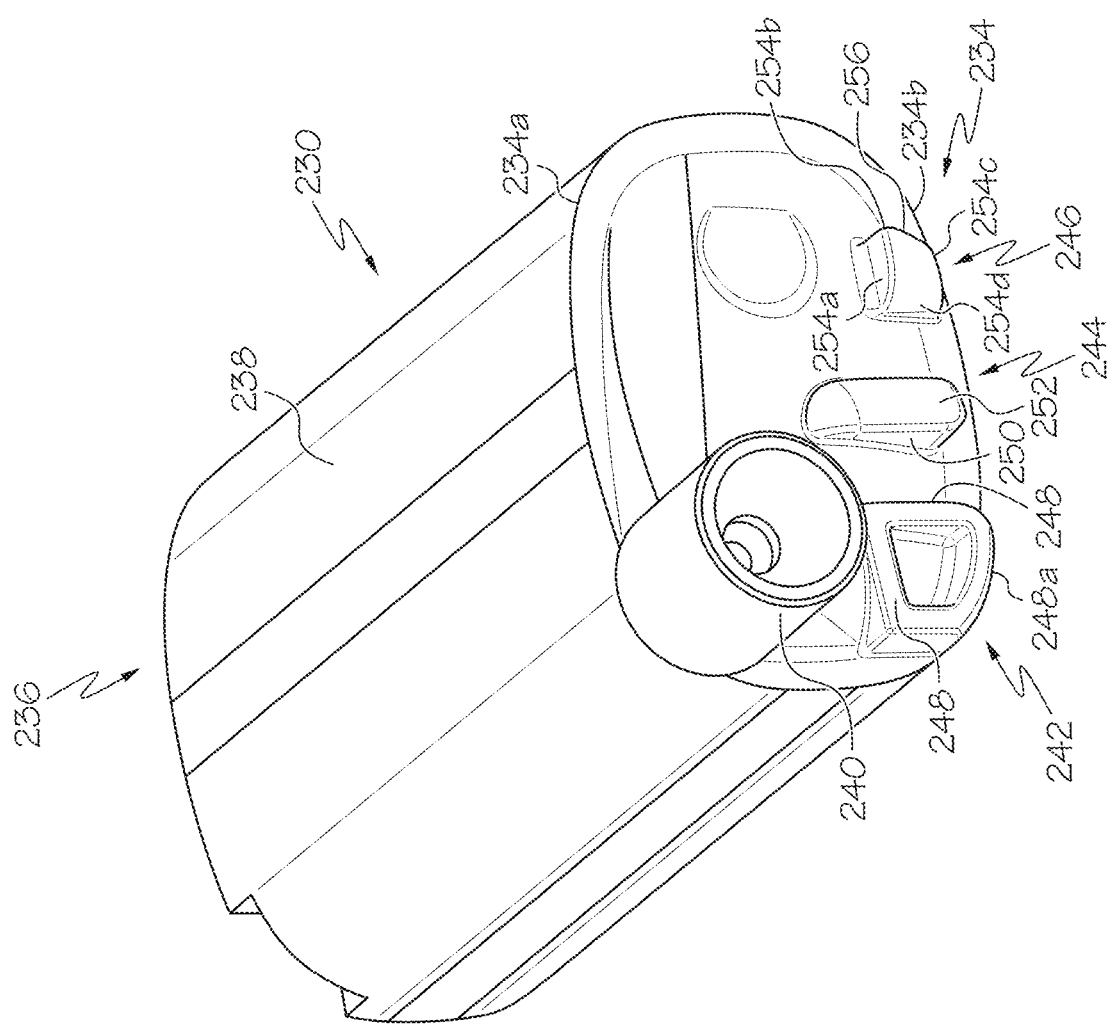

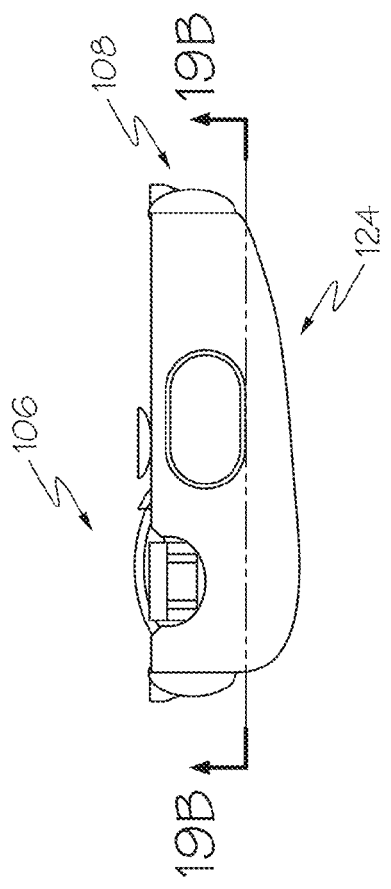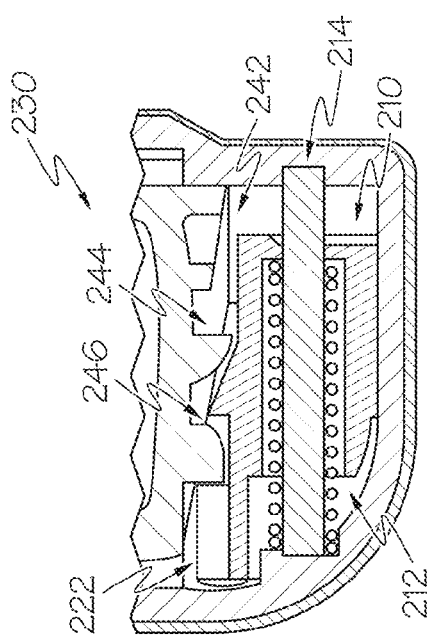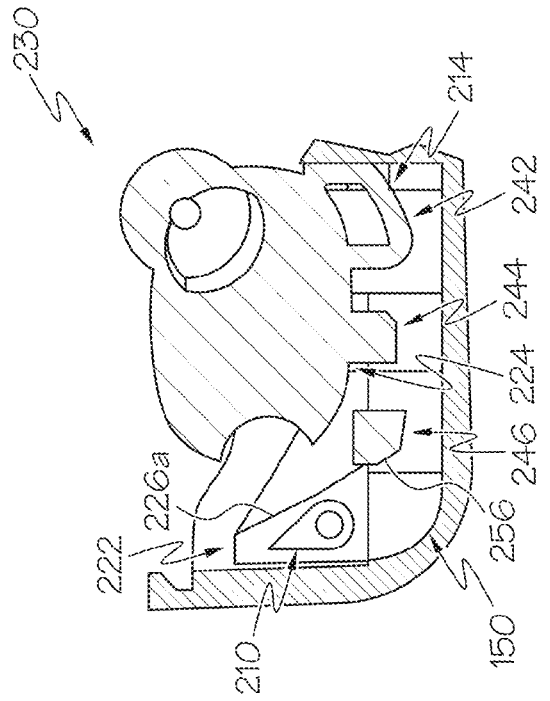

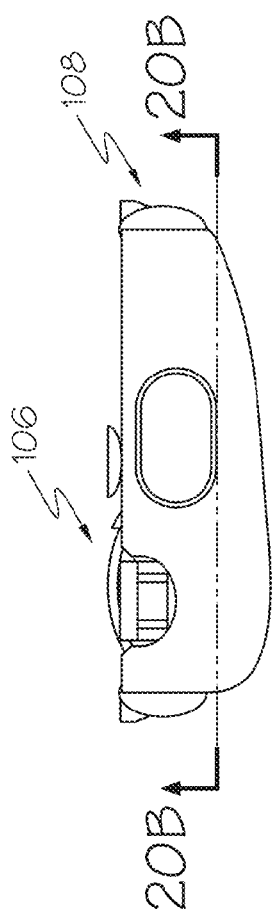
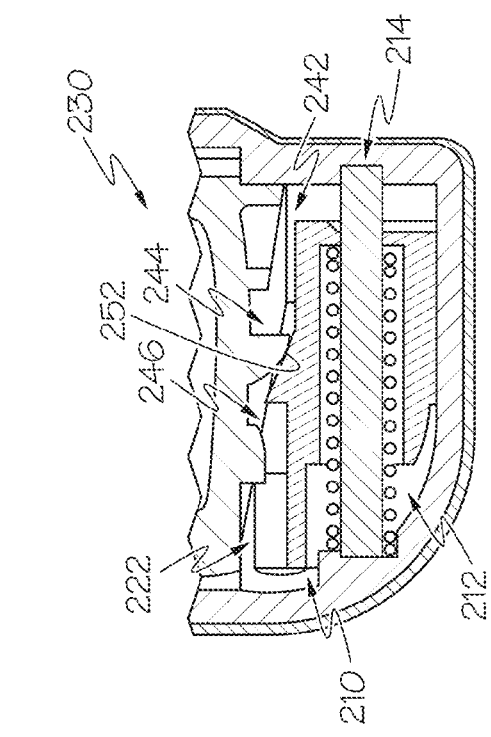
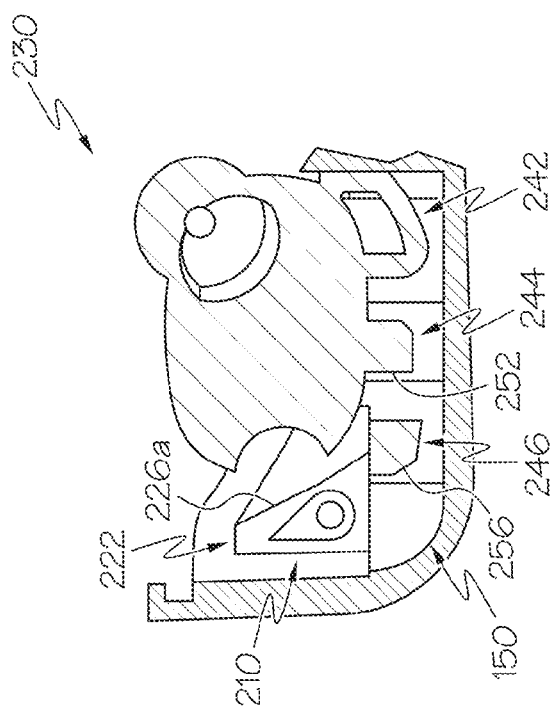
FIG. 20
FIG. 20A
FIG. 20B

SYSTEMS FOR FLUID RESERVOIR RETENTION

TECHNICAL FIELD

Embodiments of the subject matter described herein relate generally to fluid infusion devices for delivering a medication fluid to the body of a user. More particularly, embodiments of the subject matter relate to systems and methods for fluid reservoir retention.

BACKGROUND

Certain diseases or conditions may be treated, according to modern medical techniques, by delivering a medication or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion medium to the body. Alternatively, the hollow tubing may be connected directly to the patient's body through a cannula or set of micro-needles.

The fluid reservoir of an external fluid infusion device may be realized as a single-use prefilled disposable unit, a patient-filled unit, a refillable unit, or the like. The fluid reservoir for a typical fluid infusion device is implemented as a removable and replaceable component. In order to ensure proper fluid delivery, the fluid reservoir needs to be properly retained within the fluid infusion device.

Accordingly, it is desirable to provide systems and methods for retention of a removable fluid reservoir in a fluid infusion device to ensure proper insulin delivery. Furthermore, other desirable features and characteristics will become apparent from the subsequent detailed description and the appended claims, taken in conjunction with the accompanying drawings and the foregoing technical field and background.

BRIEF SUMMARY

According to various exemplary embodiments, a fluid infusion device is provided. The fluid infusion device can include a fluid reservoir having a barrel portion and a housing defining a receiving portion for removably receiving the fluid reservoir within the housing. The housing can have a first side including a first engagement system that cooperates with the barrel portion to bias the fluid reservoir relative to the housing in a direction substantially opposite a direction of fluid flow out of the fluid reservoir.

Also provided according to various exemplary embodiments is a fluid infusion device. The fluid infusion device can include a fluid reservoir having a first portion and a second portion. The fluid infusion device can also include a housing defining a receiving portion for removably receiving the fluid reservoir within the housing. The housing can have a first side adjacent to a second side. The first side can include a first engagement system that cooperates with the first portion and the second side can include a second engagement system that cooperates with the second portion. The first engagement system can include a wedge that biases the fluid reservoir relative to the housing in a direction substantially opposite a direction of fluid flow out of the fluid reservoir.

Various exemplary embodiments also provide a fluid infusion device. The fluid infusion device can include a fluid reservoir having a first portion, a second portion and a reservoir defined between the first portion and the second portion for receipt of insulin. The first portion can have a first alignment feature. The fluid infusion device can also include a first housing component including a first engagement system having a member movable by the first alignment feature between a first position and a second position. The fluid infusion device can include a second housing component coupled to the first housing component and including at least partially a second engagement system that cooperates with the second portion of the fluid reservoir. In the second position, the member can bias the fluid reservoir into contact with the second housing component.

In addition, various exemplary embodiments provide a housing for a fluid infusion device. The housing can include a first housing component including a first engagement system. The first housing component can define a first compartment and a second compartment. The first engagement system can be coupled to the second compartment and movable relative to the second compartment. The housing can also include a second housing component coupled to the first compartment of the first housing component and including a second engagement system. The second engagement system can be movable relative to the second housing component.

Various teachings provide a housing for a fluid infusion device. The housing can include a first side extending substantially perpendicular to a first end. The housing can also include a first engagement system coupled adjacent to the first end. A portion of the first engagement system can be movable relative to the first end in a direction substantially parallel to the first end. The housing can also include a second engagement system coupled to the first side. A portion of the second engagement system can be movable relative to the first side in a direction substantially perpendicular to the first side.

According to various exemplary embodiments, a fluid reservoir for use with a fluid infusion device is provided. The fluid reservoir can include a first portion having a first end and a second end. The first end can include an alignment feature and a delivery port. The fluid reservoir can include a second portion coupled to the second end of the first portion, with a portion of the second portion movable within the first portion to advance a fluid out of the delivery port. The fluid reservoir can also include a reservoir defined between the first portion and the second portion that receives the fluid.

Also provided according to various exemplary embodiments is a fluid reservoir for use with a fluid infusion device. The fluid reservoir can include a first portion having a first end and a second end. The first end can include a first alignment feature spaced apart from a second alignment feature and a delivery port adjacent to the first alignment feature. The fluid reservoir can include a second portion including a plunger and a housing. The plunger can be movable within the first portion to advance a fluid out of the delivery port and the housing can be coupled to the second end of the first portion. The fluid reservoir can include a reservoir defined between the first portion and the second portion that receives the fluid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 4A is a top perspective view of the housing of FIG. 2 with the exemplary fluid reservoir removed;

FIG. 13 is a perspective view of an exemplary barrel portion of an exemplary fluid reservoir for use with the fluid infusion device;

FIG. 19 is an end view of the housing of FIG. 2, with the fluid reservoir partially exploded above the housing;

FIG. 19A is a schematic cross-sectional view of the housing of FIG. 19, taken along line 18A-18A of FIG. 2, illustrating an exemplary partial engagement between the barrel portion of the fluid reservoir and the exemplary wedge of the reservoir retention system of the housing of FIG. 2;

FIG. 19B is a schematic cross-sectional view of the housing of FIG. 2, taken along line 19B-19B of FIG. 19, illustrating an exemplary partial engagement between the barrel portion of the fluid reservoir and the exemplary wedge of the reservoir retention system of the housing of FIG. 2;

FIG. 20 is an end view of the housing of FIG. 2, with the fluid reservoir coupled to the housing;

FIG. 20A is a schematic cross-sectional view of the housing of FIG. 20, taken along line 18A-18A of FIG. 2, illustrating an exemplary engagement between the barrel portion of the fluid reservoir and the exemplary wedge of the reservoir retention system of the housing of FIG. 2;

FIG. 20B is a schematic cross-sectional view of the housing of FIG. 2, taken along line 20B-20B of FIG. 20, illustrating an exemplary engagement between the barrel portion of the fluid reservoir and the exemplary wedge of the reservoir retention system of the housing of FIG. 2;

DETAILED DESCRIPTION

Figure 1:
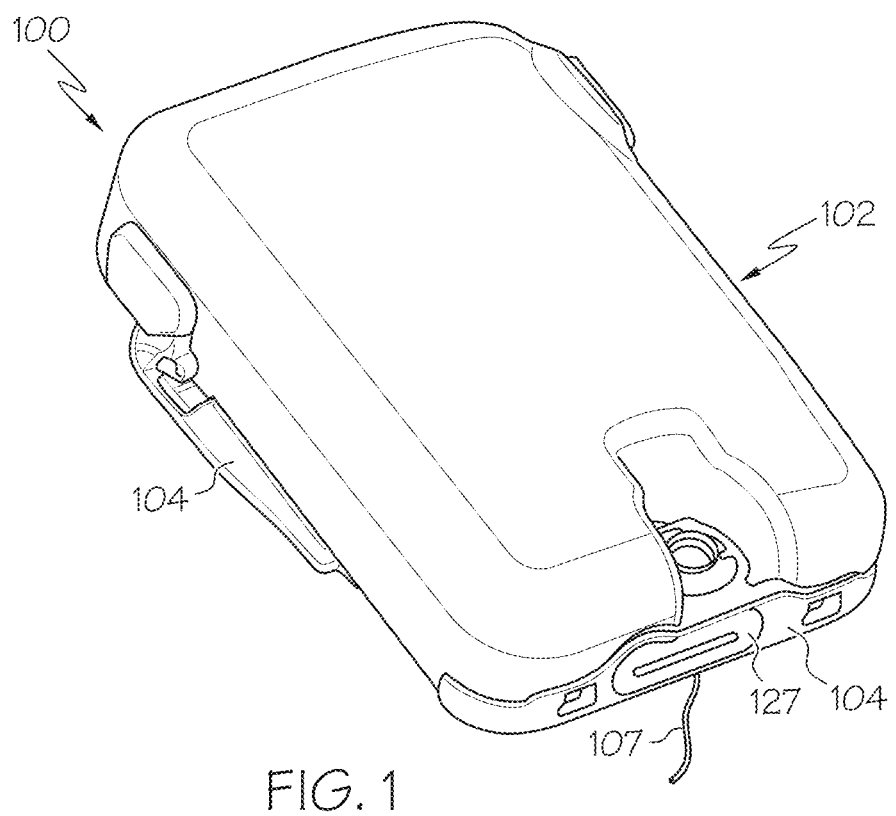
FIG. 1 is a perspective view of an exemplary embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a patient. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication No. 2009/0299290 A1; U.S. Patent Publication No. 2008/0269687; U.S. Pat. No. 7,828,764; and U.S. Pat. No. 7,905,868 (the entire content of these patent documents is incorporated by reference herein).

Figure 2:
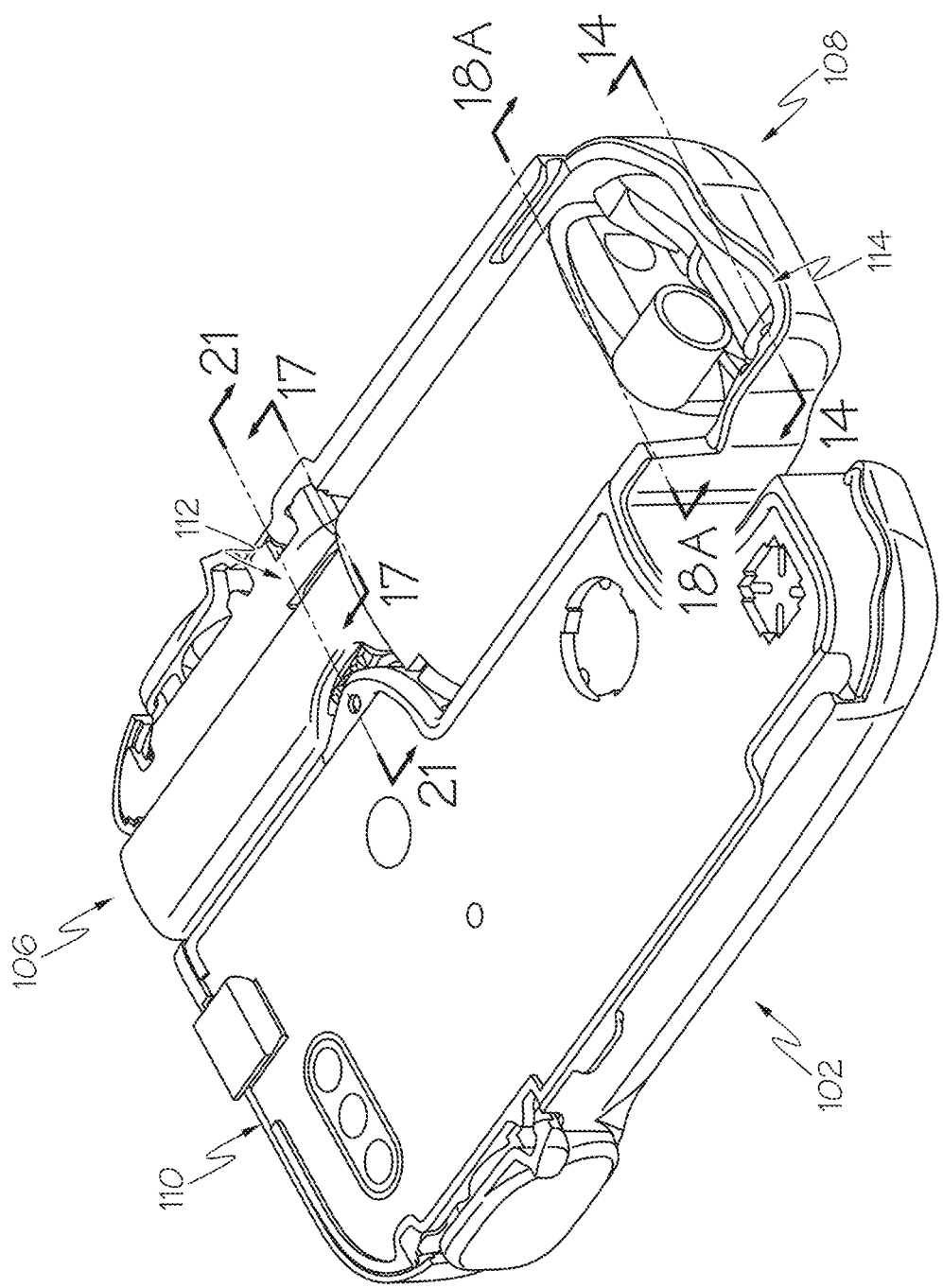
FIG. 2 is a perspective view of an exemplary housing of the fluid infusion device of FIG. 1, which includes an exemplary fluid reservoir.

FIG. 1 is a perspective view of an exemplary embodiment of a fluid infusion device 100. In one example, the fluid infusion device 100 can include a housing 102, a base plate 104 and a removable and replaceable fluid reservoir 106 (FIG. 2). In this example, the housing 102 can comprise a durable, multiple use component and the base plate 104 can comprise a consumable, single use component. It should be noted that although the housing 102 is described herein as being a durable, multiple use component, the housing 102 can be a consumable, single use component in certain embodiments. Similarly, although the base plate 104 is described herein as comprising a consumable, single use component, the base plate 104 can be a durable, multiple use component in certain embodiments. The housing 102 can be removably coupled to the base plate 104, and for the illustrated embodiment, the fluid reservoir 106 can mate with, and can be received by, the housing 102. It should be noted that the fluid reservoir 106 can mate with, and can be received by, the base plate 104 in certain embodiments. The housing 102 can cooperate with the fluid reservoir 106 to couple and retain the fluid reservoir 106 within the housing 102.

Figure 3:
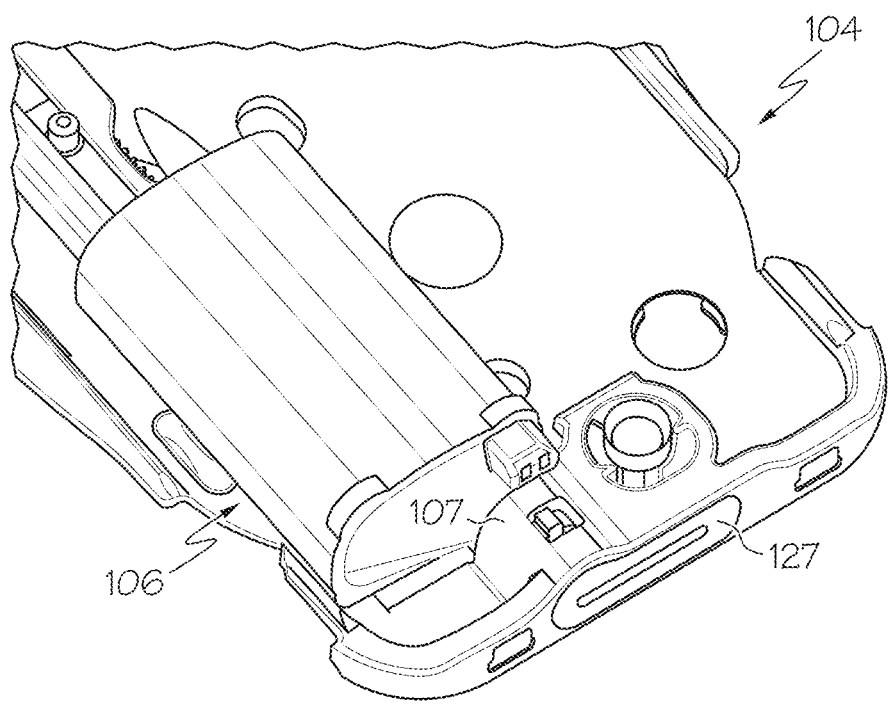
FIG. 3 is a perspective view of an exemplary base plate of the fluid infusion device of FIG. 1.

With brief reference to FIG. 3, the base plate 104 is shown with the fluid reservoir 106 in greater detail. It should be noted that the fluid reservoir 106 is illustrated in this figure to merely aid in showing the relationship between the base plate 104 and the fluid reservoir 106, but generally, the fluid reservoir 106 is retained in and coupled to the housing 102. Thus, the embodiment illustrated in FIG. 3 is merely exemplary. The base plate 104 can be temporarily adhered to the skin of the patient using, for example, an adhesive layer of material. After the base plate 104 is affixed to the skin of the patient, a suitably configured insertion device or apparatus may be used to insert a fluid delivery needle or cannula 107 (see FIG. 1) into the body of the patient. The cannula 107 can function as one part of the fluid delivery path associated with the fluid infusion device 100, as is well understood.

With reference to FIG. 1, FIG. 1 illustrates the housing 102 and the base plate 104 coupled together. The housing 102 and the base plate 104 are cooperatively configured to accommodate removable coupling of the housing 102 to the base plate 104. In practice, the housing 102 and/or the base plate 104 can include features, structures, or elements to facilitate removable coupling (e.g., pawls, latches, rails, slots, keyways, buttons, or the like). The removable nature of the housing 102 enables the patient to replace the fluid reservoir 106 as needed. Moreover, the housing 102 can be removed (while leaving the base plate 104 adhered to the patient) to allow the patient to swim, shower, bathe, and participate in other activities that might otherwise damage or contaminate the housing 102. When the housing 102 is removed from the base plate 104, the fluid flow path is broken.

Figure 4B:
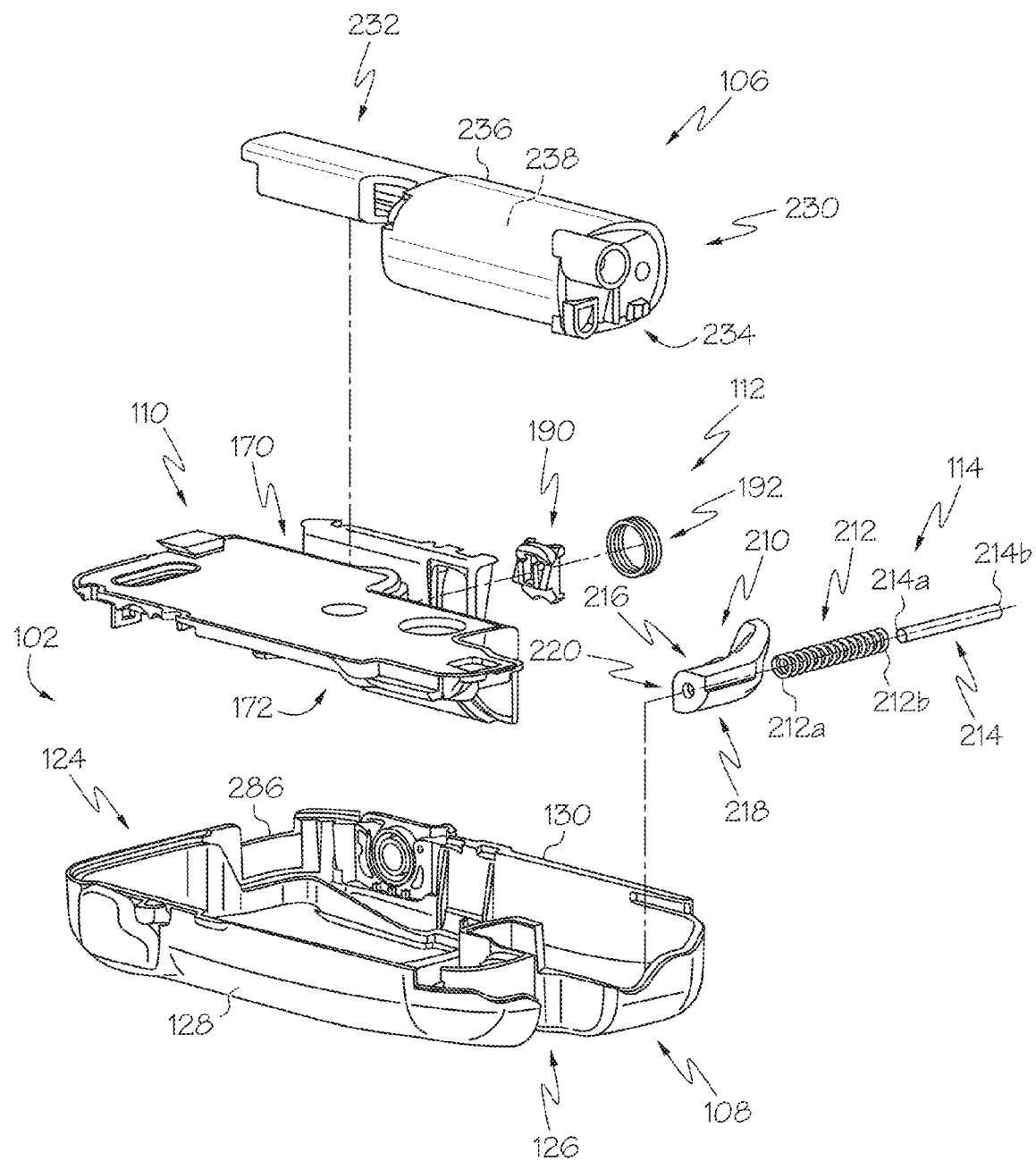
FIG. 4B is a partially exploded view of the housing of FIG. 2.

With reference to FIGS. 2, 4A and 4B, the housing 102 is shown in more detail. The housing 102 can include a first or top housing component 108, a second or bottom housing component 110, a pinion engagement system 112 (FIGS. 4A and 4B) and a reservoir engagement system 114. Further, the housing 102 can include, among other components, a drive motor, a battery, a rack and pinion drive system that cooperates with the fluid reservoir, and suitable circuitry to control those components. Further detail regarding these components can be found in commonly assigned U.S. Patent Publication No. 2011/0160655, U.S. Patent Publication No. 2011/010654, U.S. Patent Publication No. 2011/010666, and U.S. Pat. No. 7,905,868, each of which is incorporated by reference herein. These components can generally be housed in a cavity formed between the top housing component 108 and the bottom housing component 110.

Figure 5:
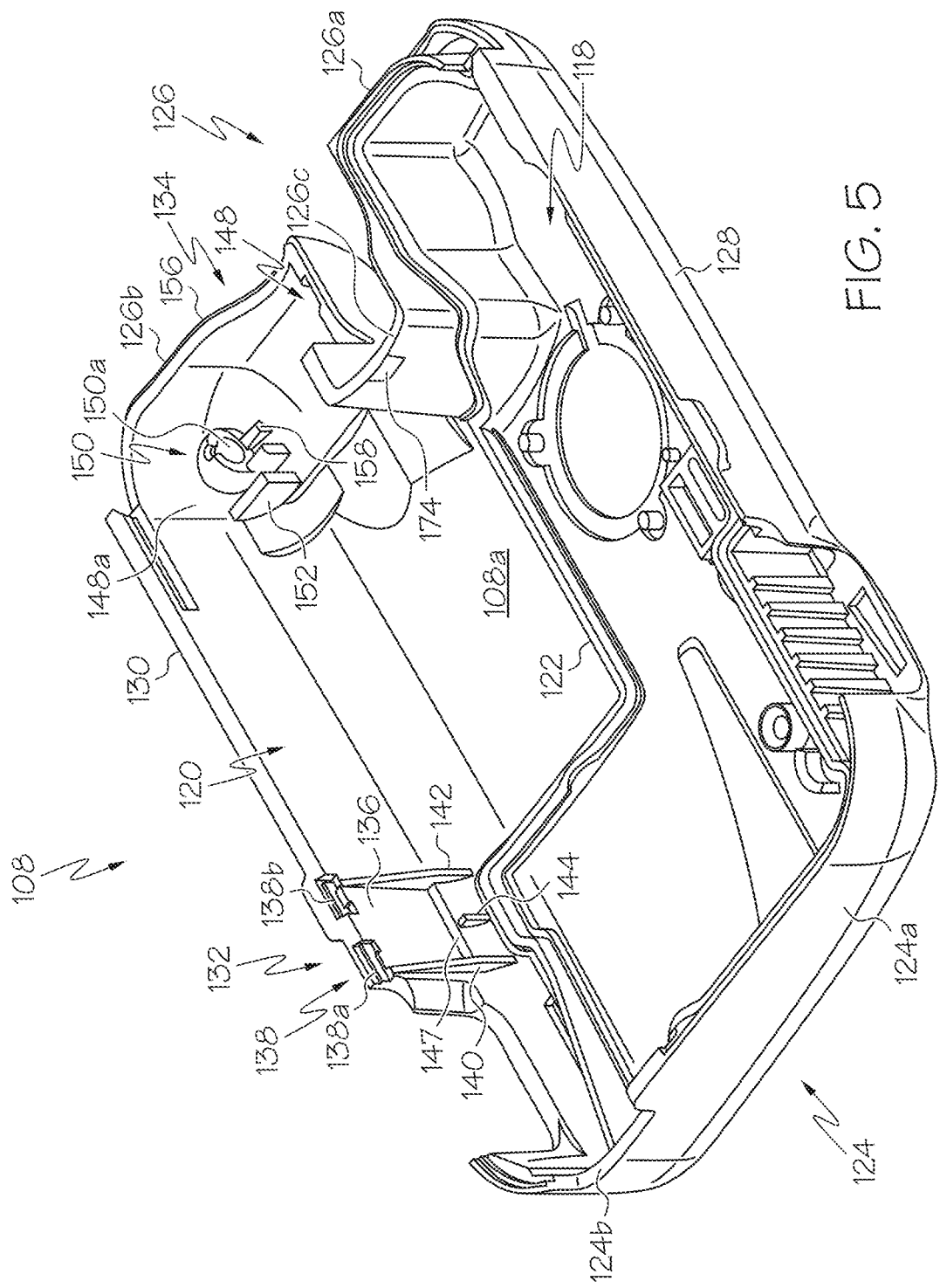
FIG. 5 is a perspective view of an exemplary top housing component of the housing of FIG. 2.
Figure 6:
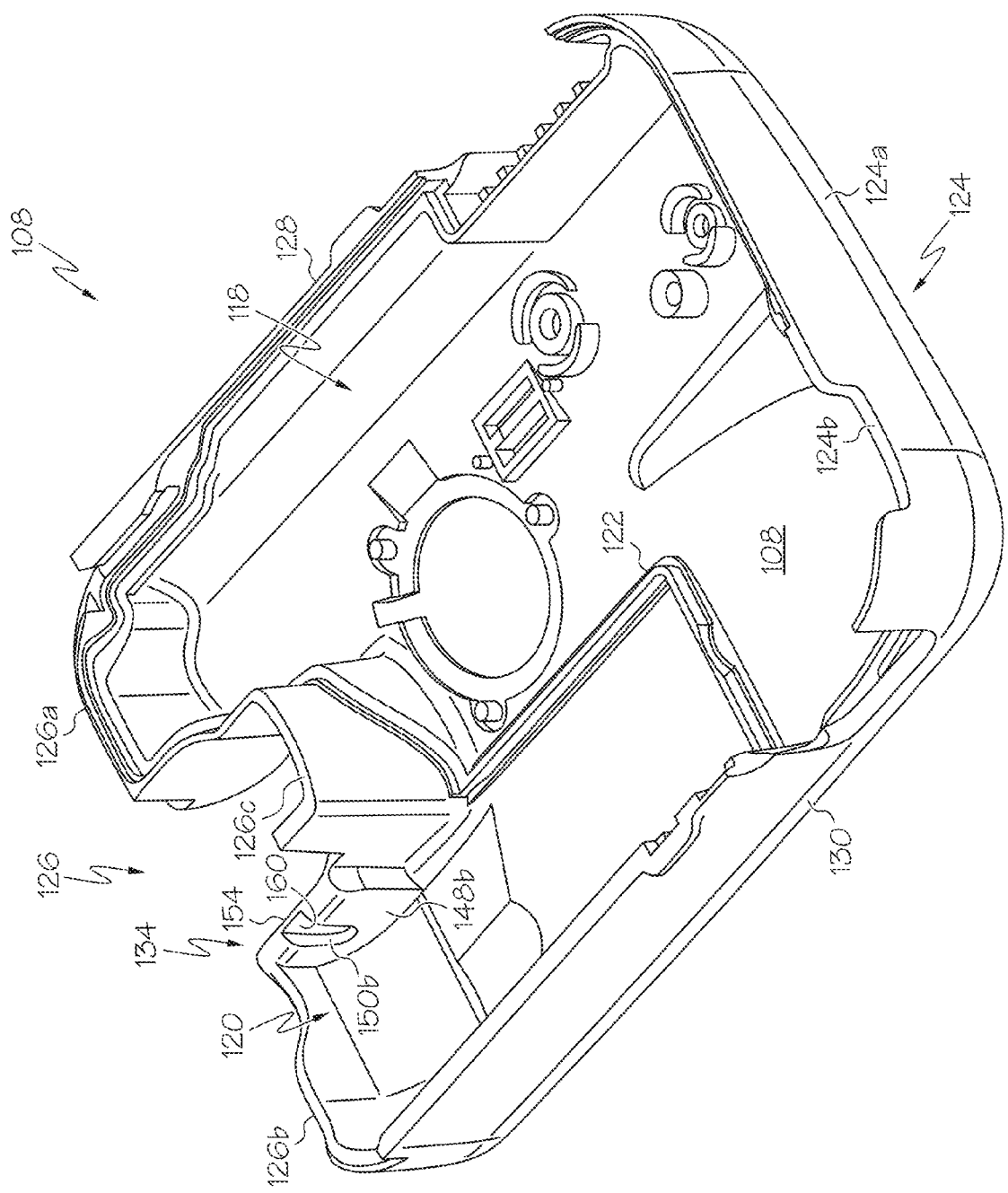
FIG. 6 is another perspective view of the exemplary top housing component of FIG. 5.

In one example, with reference to FIGS. 5 and 6, the top housing component 108 can include a first compartment 118 and a second compartment 120, which can be separated by a protrusion or wall 122 defined along a surface 108a of the top housing component 108. In one example, the wall 122 can extend from a first side or first end 124 to a second side or second end 126 of the top housing component 108. The first compartment 118 can be defined by the wall 122, a portion 124a of the first end 124, a first portion 126a of the second end 126 and a first side 128 of the top housing component 108. The second compartment 120 can be defined by the wall 122, a second portion 124b of the first end 124, a second portion 126b of the second end 126 and a second side 130 of the top housing component 108. It should be noted that this arrangement of the first compartment 118 and second compartment 120 is merely exemplary, as any suitable arrangement or configuration of the first compartment 118 and second compartment 120 could be employed, and further, the top housing component 108 could include more than two compartments, or could include a single compartment, if desired. In one example, the first compartment 118 can be defined substantially on a side of a longitudinal axis of the top housing component 108, and the second compartment 120 can be defined substantially or entirely on an opposite side of the longitudinal axis of the top housing component 108.

Further, it should be understood that in addition to the first compartment 118, second compartment 120 and wall 122, the top housing component 108 can include various other features and components that can enable the housing 102 to cooperate with the base plate 104 to deliver insulin to a user. For example, the top housing component 108 can include features that enable the housing 102 to be removably coupled to the base plate 104, etc. In addition, the first portion 126a and the second portion 126b of the second end 126 can be spaced apart from each other by a third portion 126c, which can be indented or positioned towards the first end 124 more than the first portion 126a and the second portion 126b. This spacing or configuration can enable the fluid path to be established between the housing 102 and the patient. In this regard, a mounting cap 127 including a sealing element (FIG. 1) can be received within the recess defined by the third portion 126c, which can aid in establishing a fluid connection with the patient, as discussed in commonly assigned U.S. application Ser. No. 13/399,878, incorporated by reference herein.

With continued reference to FIGS. 5 and 6, the first compartment 118 can include various features for coupling the bottom housing component 110 to the top housing component 108, and can also include features that can cooperate with other components associated with the housing 102, such as the drive motor, battery, etc. Generally, the bottom housing component 110 can be coupled to the first compartment 118 of the top housing component 108 to define a cavity for receipt of the other components of the housing 102. In one example, the bottom housing component 110 can be coupled to the first compartment 118 to as to substantially cover the first compartment 118 (FIG. 2). It should be noted, however, that the bottom housing component 110 can be coupled to and can cover, all or a portion of the top housing component 108.

With reference to FIGS. 5 and 6, the second compartment 120 can include a pinion engagement portion 132 and a reservoir engagement portion 134. In one example, the pinion engagement portion 132 can be defined on the second side 130 of the top housing component 108, and the reservoir engagement portion 134 can be defined in the second portion 126b of the second end 126. The pinion engagement portion 132 can include a recess 136 and at least one coupling surface 138. In one exemplary embodiment, the recess 136 can be defined between a first partition 140, a second partition 142 and a projection 144. It should be noted that the use of the first partition 140, second partition 142 and projection 144 is merely exemplary, as the recess 136 can be defined between one or more partitions. Generally, the first partition 140 can be spaced apart from the second partition 142 to define the recess 136. The recess 136 can receive a portion of the pinion engagement system 112, as will be discussed herein. The projection 144 can be spaced generally below and between the first partition 140 and second partition 142 to constrain the portion of the pinion engagement system 112 between the first partition 140 and second partition 142. In addition, if desired, a ledge 147 can be defined in the second side 130 between the first partition 140 and second partition 142 to further support the portion of the pinion engagement system 112.

In one example, the at least one coupling surface 138 can define a first coupling surface 138a and a second coupling surface 138b. The first coupling surface 138a can be spaced apart from the second coupling surface 138b, and can be configured to aid in coupling the bottom housing component 110 to the top housing component 108. In one example, the first coupling surface 138a and second coupling surface 138b can define a recess, which can receive a suitable adhesive along with a portion of the bottom housing component 110 for adhesively coupling the bottom housing component 110 to the top housing component 108. It should be noted that any suitable technique can be used to couple the bottom housing component 110 to the top housing component 108, such as the use of mechanical fasteners, press-fitting, etc.

The reservoir engagement portion 134 can include at least one contact surface 148, at least one retaining bore 150 and a constraining wall 152. In one example, the at least one contact surface 148 can include a first contact surface 148a (FIG. 5) and a second contact surface 148b (FIG. 6). The first contact surface 148a can be spaced apart from and substantially opposite the second contact surface 148b. In this regard, the first contact surface 148a can be formed on the second side 130, and the second contact surface 148b can be formed on a sidewall 154 of the second portion 126b of the second end 126. The first contact surface 148a and second contact surface 148b can contact a portion of the reservoir engagement system 114 to constrain the movement of the reservoir engagement system 114, as will be discussed herein.

The at least one retaining bore 150 can retain a portion of the reservoir engagement system 114. In one example, the at least one retaining bore 150 can include a first retaining bore 150a (FIG. 5), which can be spaced apart from and substantially opposite a second retaining bore 150b (FIG. 6). In this example, the first retaining bore 150a can be formed on the second side 130, and the second retaining bore 150b can be formed on the sidewall 154 of the second portion 126b of the second end 126. Generally, the first retaining bore 150a can be formed between the first contact surface 148a and a sidewall 156 of the second portion 126b. Similarly, the second retaining bore 150b can be formed between the second contact surface 148b and the sidewall 156 of the second portion 126b. The sidewall 156 of the second end 126 can also contact a portion of the reservoir engagement system 114 to constrain the movement of the reservoir engagement system 114.

In one example, the first retaining bore 150a can include a lip 158, which can extend circumferentially about a least a portion of the first retaining bore 150a to aid in guiding and retaining a portion of the reservoir engagement system 114. It should be noted that the lip 158 is merely exemplary, as the first retaining bore 150a can comprise a recess defined within the second side 130. The second retaining bore 150b can comprise a recess defined within the sidewall 154 of the second end 126, and can include a slot 160. The slot 160 can assist in coupling the portion of the reservoir engagement system 114 to the top housing component 108. In one example, the slot 160 can receive an adhesive to fixedly couple a portion of the reservoir engagement system 114 to the top housing component 108. It should be noted that the use of the slot 160 is merely exemplary, as any suitable technique could be used to fixedly couple the portion of the reservoir engagement system 114 to the top housing component 108, such as a mechanical fastener, press-fit, etc.

With reference to FIG. 5, the constraining wall 152 can be defined adjacent to the first retaining bore 150a. The constraining wall 152 can project upwardly from the surface 108a of the top housing component 108, and can extend from the second side 130 towards the sidewall 154. The constraining wall 152 can have a height selected to enable the constraining wall 152 to contact a portion of the reservoir engagement system 114 to constrain the rotational movement of the reservoir engagement system 114. It should be noted that the use and configuration of the constraining wall 152 is merely exemplary, as any suitable technique could be used to constrict the rotational movement of the reservoir engagement system 114, including modifications to the reservoir engagement system 114 itself.

The wall 122 can cooperate with the bottom housing component 110 to couple the top housing component 108 to the bottom housing component 110. In one example, the wall 122 can comprise a tongue portion of a tongue and groove adhesive joint, which can cooperate with a corresponding portion of the bottom housing component 110. The wall 122 can have any suitable height, and for example, can have a varying height, which can correspond to the bottom housing component 110. It should be noted that the wall 122 and the height of the wall 122 is merely exemplary, the bottom housing component 110 could cooperate directly with the surface 108a, if desired.

Figure 7:
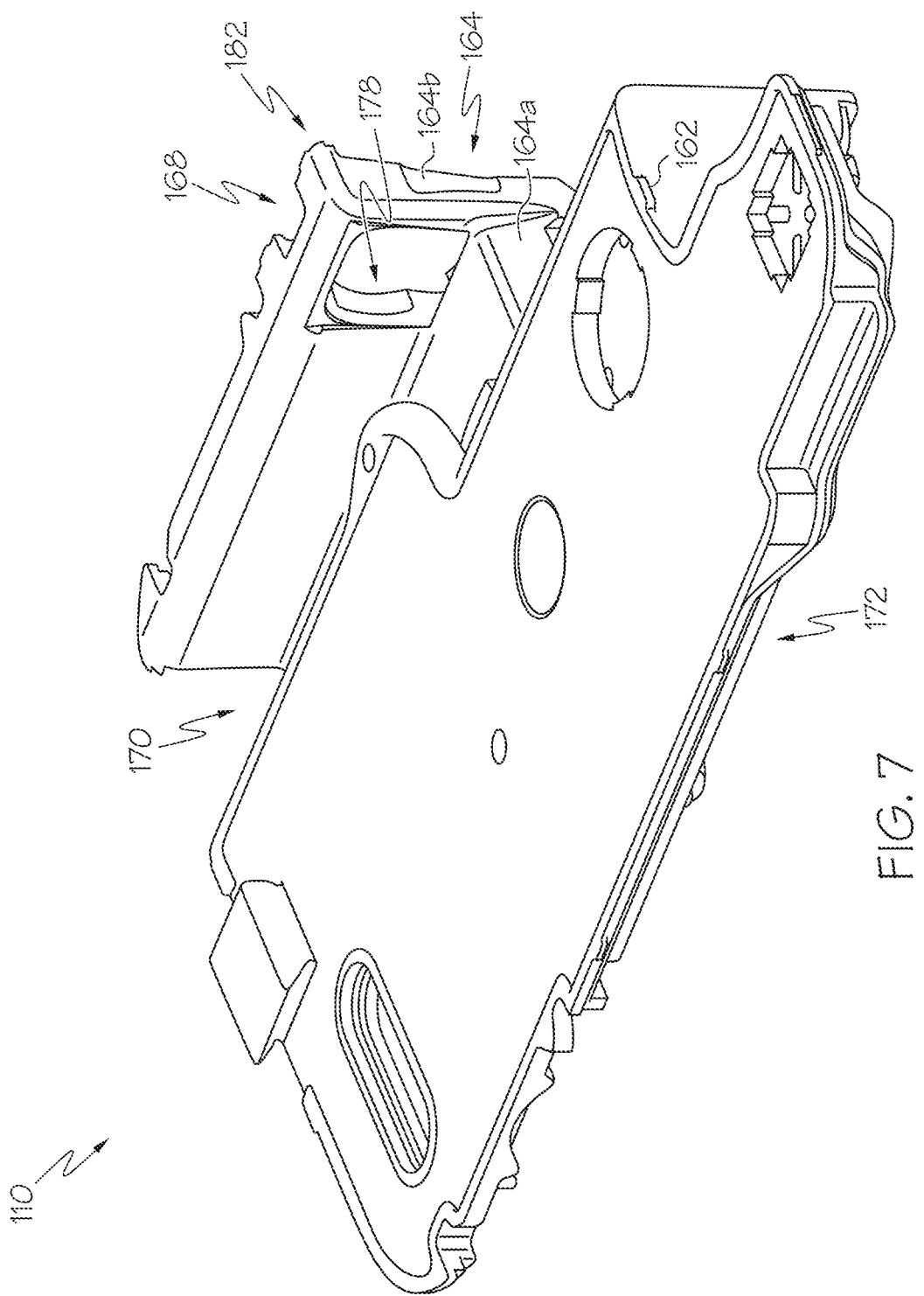
FIG. 7 is a top perspective view of an exemplary bottom housing component of the housing of FIG. 2.
Figure 8:
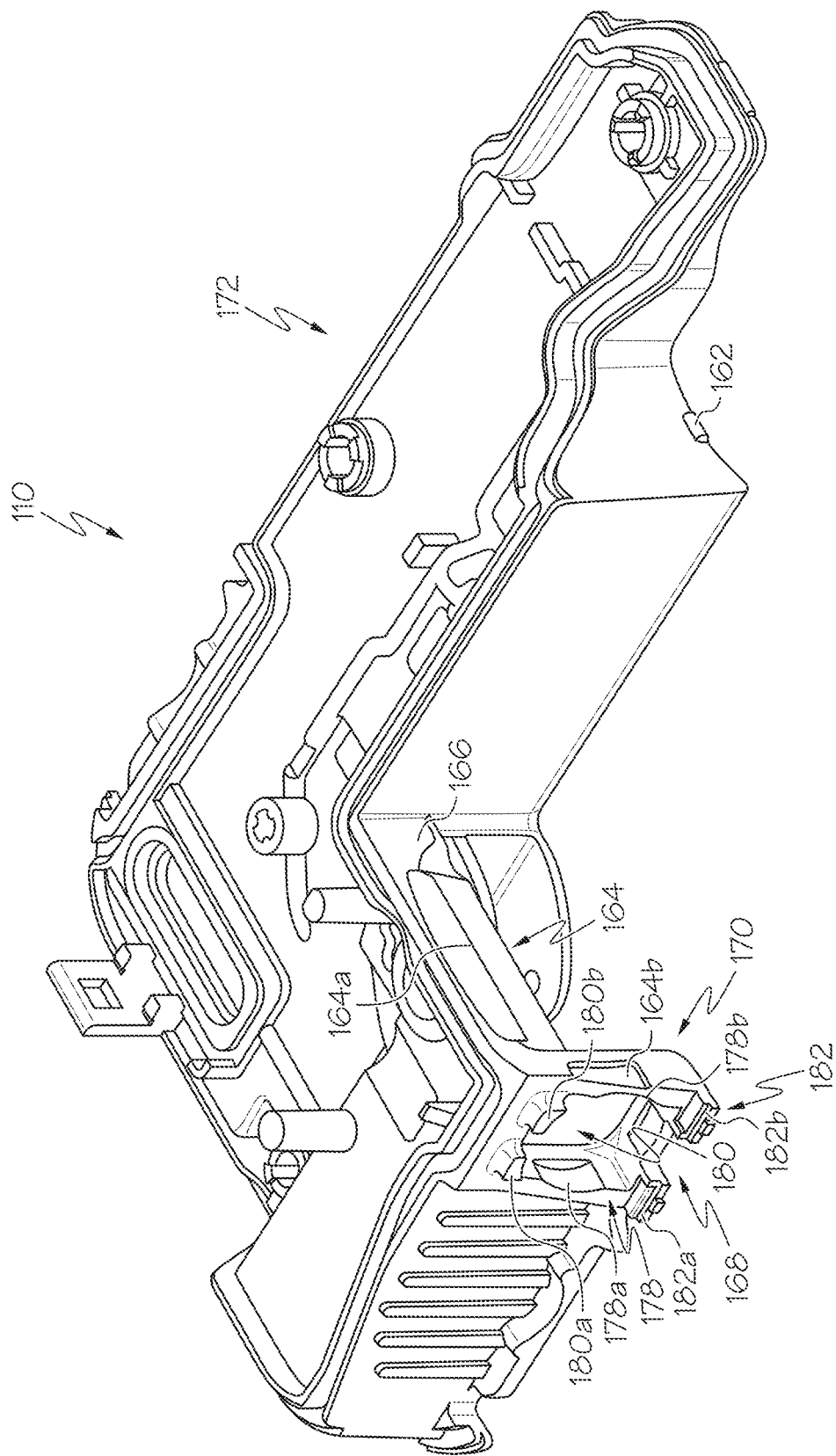
FIG. 8 is a bottom perspective view of the exemplary bottom housing component of FIG. 7.

With reference to FIGS. 7 and 8, the second or bottom housing component 110 can be coupled to the top housing component 108. The bottom housing component 110 can include a perimeter, which can include at least one interference 162, at least one relief 164, at least one contact face 166 (FIG. 8) and a pinion engagement portion 168. It should be noted that although the at least one interference 162, at least one relief 164, at least one contact face 166 and pinion engagement portion 168 are described and illustrated herein as being disposed along the perimeter of the bottom housing component 110, the at least one interference 162, at least one relief 164, at least one contact face 166 and pinion engagement portion 168 could be formed at any selected location on the bottom housing component 110. The bottom housing component 110 can also define a reservoir receiving portion 170 and a component receiving portion 172.

The at least one interference 162 can assist in coupling the bottom housing component 110 to the top housing component 108. In one example, the at least one interference 162 can mate with a recessed slot 174 (FIG. 5) defined in the third portion 126c of the second end 126 to assist in coupling the bottom housing component 110 to the top housing component 108. It should be noted that while one interference 162 is illustrated and discussed herein, multiple interferences 162 can be located about the perimeter of the bottom housing component 110 to facilitate coupling the bottom housing component 110 to the top housing component 108. Further, the use of the at least one interference 162 is merely exemplary, as any suitable technique could be used in guiding or aligning the bottom housing component 110 within the top housing component 108, such as rails, dovetails, etc.

The at least one relief 164 can provide clearance for a portion of the fluid reservoir 106. In one example, the at least one relief 164 can comprise a first relief 164a and a second relief 164b. The first relief 164a can be defined in the reservoir receiving portion 170, and the second relief 164b can be defined in the reservoir receiving portion 170 adjacent to the pinion engagement portion 168. Generally, the at least one relief 164 can provide clearance to accommodate for manufacturing tolerances in the production of the fluid reservoir 106. It should be noted that the use of the at least one relief 164 is merely exemplary, as other manufacturing processes may not require the use of at least one relief 164.

With reference to FIG. 8, the at least one contact face 166 can be defined adjacent to the first relief 164a. The at least one contact face 166 can contact a portion of the fluid reservoir 106 to limit the travel of the fluid reservoir 106 relative to the housing 102. It should be noted that although one contact face 166 is illustrated and described herein, the housing 102 can include any number of contact faces 166 that can restrict the movement of the fluid reservoir 106.

With reference to FIGS. 7 and 8, the pinion engagement portion 168 can be defined in the reservoir receiving portion 170. The pinion engagement portion 168 can define a channel, which can receive the pinion engagement system 112. The pinion engagement portion 168 can include at least one spring guide 178, at least one retention flange 180 and at least one coupling flange 182. Generally, the pinion engagement portion 168 can be configured such that at least a portion of the pinion engagement system 112 can be retained in the channel to aid in coupling the pinion engagement system 112 to the housing 102.

With reference to FIG. 8, the at least one spring guide 178 can include a first spring guide 178a and a second spring guide 178b, which can be formed substantially opposite each other about a perimeter of the pinion engagement portion 168. In one example, the first spring guide 178a and second spring guide 178b can be at least partially circumferential to receive a portion of the pinion engagement system 112, as will be discussed herein.

With continued reference to FIG. 8, the at least one retention flange 180 can include a first retention flange 180a and a second retention flange 180b. The first retention flange 180a and second retention flange 180b can have any shape, which can correspond to a portion of the pinion engagement system 112, and can be formed near the perimeter of the pinion engagement portion 168. Generally, the first retention flange 180a and second retention flange 180b can be formed on the bottom housing component 110 so as to be near the surface 108a of the top housing component 108 when the bottom housing component 110 is coupled to the top housing component 108.

The at least one coupling flange 182 in one example, can comprise a first coupling flange 182a and a second coupling flange 182b. The first coupling flange 182a and second coupling flange 182b can mate with a corresponding one of the first coupling surface 138a and second coupling surface 138b to couple the bottom housing component 110 to the top housing component 108. Generally, the first coupling flange 182a and second coupling flange 182b can be shaped to enable an adhesive to be positioned between the first coupling flange 182a and second coupling flange 182b and respective ones of the first coupling surface 138a and a second coupling surface 138b to adhesively couple the bottom housing component 110 to the top housing component 108, however, as discussed, any suitable technique could be employed to couple the bottom housing component 110 to the top housing component 108.

With reference to FIG. 7, the reservoir receiving portion 170 can receive a portion of the fluid reservoir 106 when the fluid reservoir 106 is coupled to the housing 102. In one example, the reservoir receiving portion 170 can comprise a substantially U-shaped channel, which can cooperate with the second compartment 120 of the top housing component 108 to enable the fluid reservoir 106 to be coupled to the housing 102. The substantially U-shaped channel defined by the reservoir receiving portion 170 can be in communication with the pinion engagement portion 168 to enable the pinion engagement system 112 to contact a portion of the fluid reservoir 106, as will be discussed herein. The component receiving portion 172 can receive the other components of the housing 102, such as the battery, circuitry, etc. At least a portion of the component receiving portion 172 can be received within the first compartment 118 of the top housing component 108.

Figure 10:
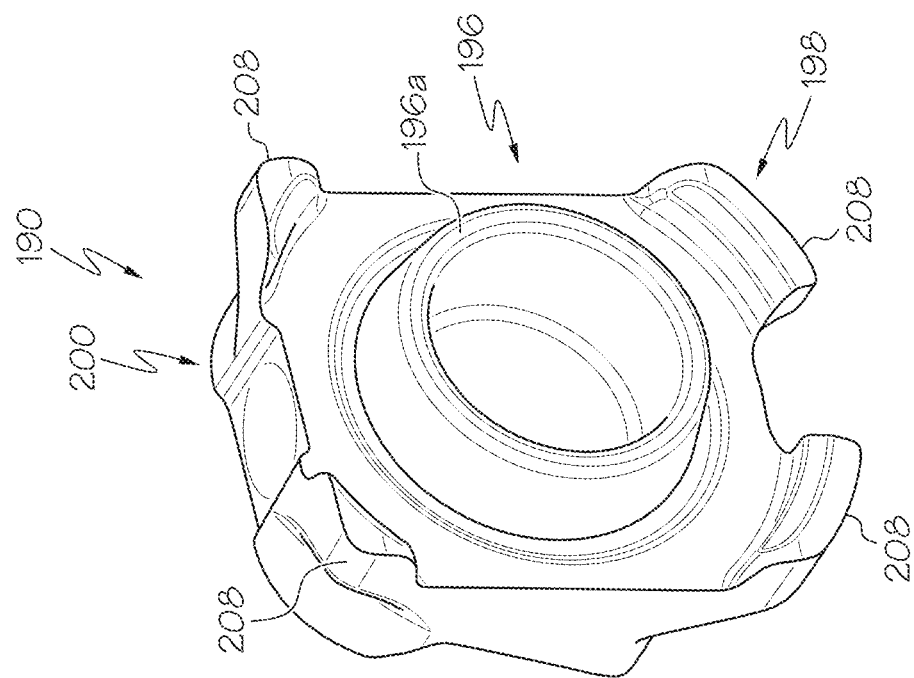
FIG. 10 is a rear perspective view of the exemplary snap housing of FIG. 9.
Figure 9:
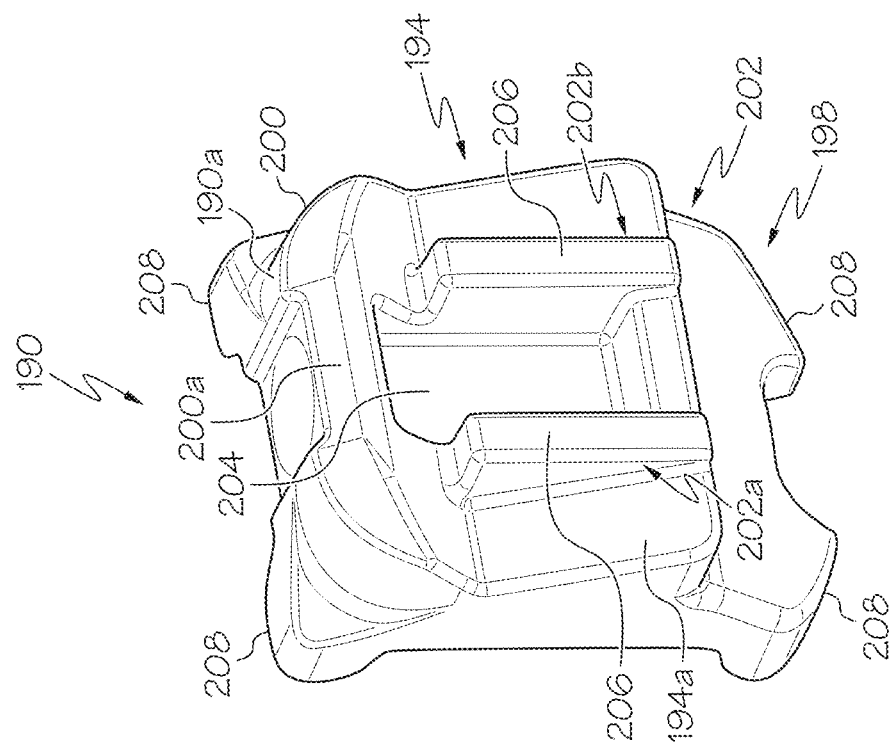
FIG. 9 is a front perspective view of an exemplary snap housing of the pinion engagement system of the housing of FIG. 2.

With reference now to FIG. 4B, the pinion engagement system 112 is shown. In one example, the pinion engagement system 112 can include a snap housing 190 and a biasing member 192. The snap housing 190 can be received in the pinion engagement portion 168 of the bottom housing component 110. With reference to FIGS. 9 and 10, the snap housing 190 can include a first side 194 (FIG. 9), a second side 196 (FIG. 10) and a perimeter 198. With reference to FIG. 9, the first side 194 can include a lip 200, at least one projection 202 and a cavity 204. The cavity 204 can cooperate with a portion of the fluid reservoir 106, and can also aid in forming the snap housing 190. In one example, the cavity 204 can aid in forming the snap housing 190 when the snap housing 190 is formed using injection molding. It should be noted that the snap housing 190 could be formed through any suitable forming technique, and thus, the use of injection molding and the cavity 204 is merely exemplary. The lip 200 can be defined adjacent to a top surface 190a of the snap housing 190, between the top surface 190a and the at least one projection 202. The lip 200 can cooperate with a portion of the fluid reservoir 106 to removably couple the fluid reservoir 106 to the bottom housing component 110. The lip 200 can be defined to intersect a longitudinal axis of the snap housing 190 and can include a slight curvature, however, the lip 200 can have any desired shape. The lip 200 can include a relief 200a, which can facilitate the forming of the snap housing 190 through injection molding. It should be noted that the relief 200a is merely exemplary, and that any suitable technique could be used to manufacture the snap housing 190. As will be discussed, the snap housing 190 can move or slide relative to the pinion engagement portion 168 to aid in coupling the fluid reservoir 106 to the housing 102. The lip 200 can generally extend outwardly from the first side 194 for a distance greater than the at least one projection 202 to aid in providing feedback to the user upon coupling of the fluid reservoir 106 to the housing 102.

The at least one projection 202 can contact a portion of the fluid reservoir 106 to create an audible indicator that the fluid reservoir 106 is coupled to the housing 102. In one example, the at least one projection 202 can comprise a first projection 202a and a second projection 202b. The first projection 202a and the second projection 202b can extend outwardly away from the first side 194, and can each include a contact face 206. The contact faces 206 can contact the portion of the fluid reservoir 106, as will be discussed herein. In addition, the first projection 202a and the second projection 202b can be inclined relative to a surface 194a of the first side 194, to provide clearance to another portion of the fluid reservoir 106 such that generally only the contact faces 206 contact the fluid reservoir 106.

With reference to FIG. 10, the second side 196 of the snap housing 190 can include a spring guide 196a. In one example, the spring guide 196a can comprise an annular projection, which can extend outwardly from a surface of the second side 196. It will be understood, however, that the spring guide 196a is merely exemplary, as the second side 196 could have any desired shape and configuration.

The perimeter 198 of the snap housing 190 can include at least one or a plurality of retention flanges 208. The retention flanges 208 can be spaced about the perimeter of the snap housing 190, and can cooperate with the first retention flange 180a and second retention flange 180b of the bottom housing component 110 to retain the snap housing 190 within the pinion engagement portion 168. It should be noted that while a plurality of retention flanges 208 are illustrated and described herein, the snap housing 190 could be retained within the pinion engagement portion 168 via any suitable technique, including, but not limited to, a dovetail arrangement or slot and rail. As best illustrated in FIG. 10, the retention flanges 208 can also cooperate with the spring guide 196a to guide the biasing member 192, and to couple the biasing member 192 to the snap housing 190.

With regard to FIG. 4B, the biasing member 192 can bias the snap housing 190 in the channel defined by the pinion engagement portion 168. In this regard, the biasing member 192 can be positioned between the top housing component 108 and the second side 196 of the snap housing 190. Generally, the biasing member 192 can bias the snap housing 190 such that the snap housing 190 extends through the channel of the pinion engagement portion 168 into a portion of the reservoir receiving portion 170 in a first position. The application of force against the snap housing 190, by the insertion of the fluid reservoir 106 into the housing 102, for example, can overcome the force of the biasing member 192 and can cause the snap housing 190 to move from the first position to a second position within the channel of the pinion engagement portion 168 to allow the insertion of the fluid reservoir 106. In other words, the snap housing 192 can move relative to the bottom housing component 110, in a direction substantially perpendicular to the second side 130 of the housing 102. In one example, the biasing member 192 can comprising a wave spring, but the biasing member 192 can comprise any suitable biasing member, including, but not limited to, a coil spring.

Figure 14:
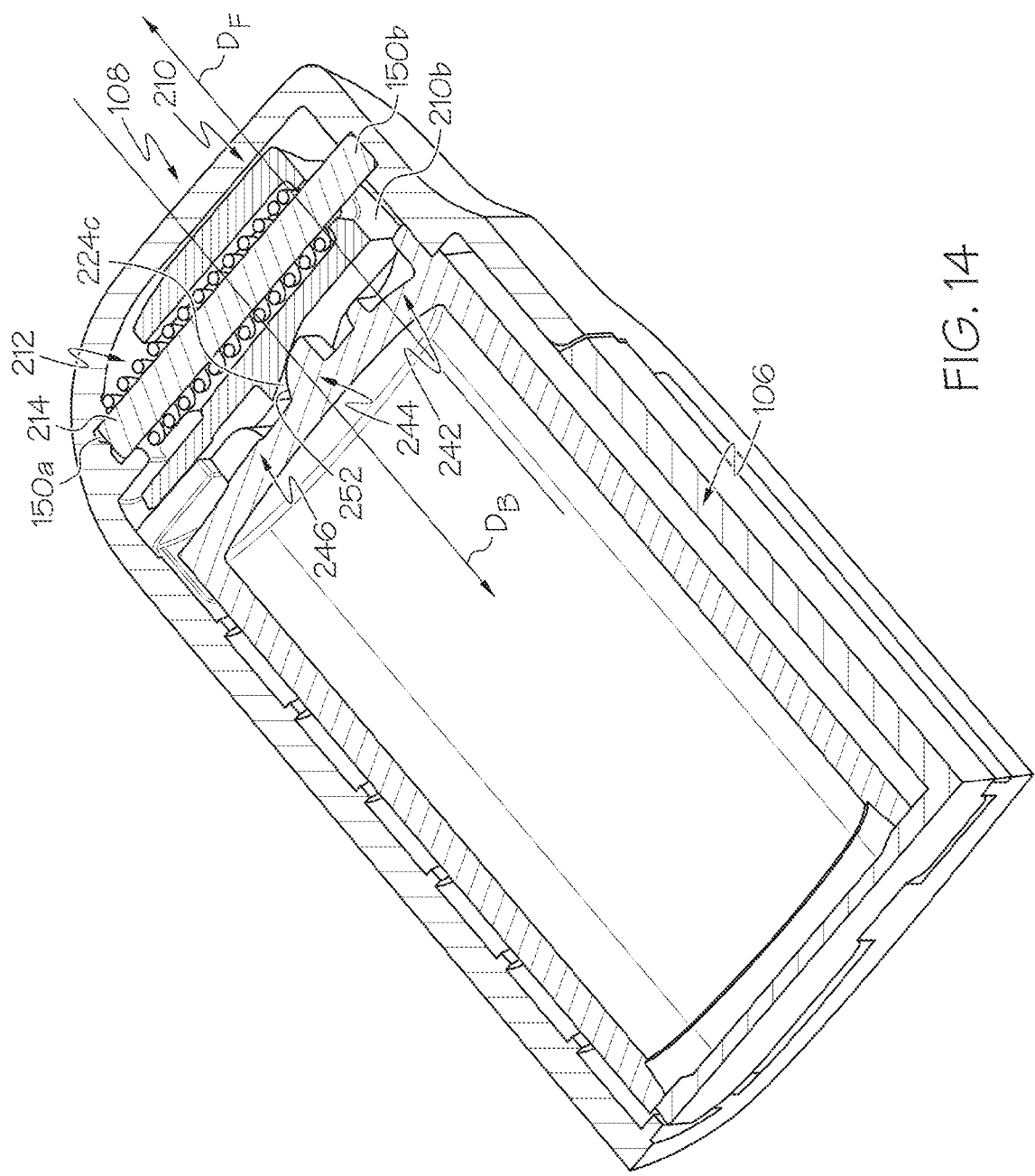
FIG. 14 is a cross-sectional view of the housing of FIG. 2, taken along line 14-14 of FIG. 2, illustrating an exemplary engagement between the fluid reservoir and the reservoir retention system of the housing of FIG. 2.

The reservoir engagement system 114 can be coupled to the reservoir engagement portion 134 of the top housing component 108. The reservoir engagement system 114 can be coupled to and can contact a portion of the fluid reservoir 106 to couple the fluid reservoir 106 to the housing 102. Generally, the reservoir engagement system 114 can engage the fluid reservoir 106 such that the fluid reservoir 106 is biased in the housing 102 in a direction opposite the flow of fluid out of the fluid reservoir 106. Thus, the reservoir engagement system 114 can be movable between a first position, in which the fluid reservoir 106 is not coupled to the housing 102 (FIG. 4A), and a second position, in which the fluid reservoir 106 is coupled to the housing 102 and biased in the direction opposite of fluid flow (FIG. 14). Generally, the fluid reservoir 106 is retained in the housing 102 under a load to assist in detecting an occlusion in the fluid pathway defined by and between the fluid reservoir 106 and the cannula 107. In this regard, by biasing the fluid reservoir 106 within the housing 102, pressure can build within the fluid reservoir 106 upon the occurrence of an occlusion, which can be detected by components and circuitry coupled to the housing 102, as is generally known. The reservoir engagement system 114 can include a member or wedge 210, a reservoir biasing member 212 and a retention member 214.

Figure 12:
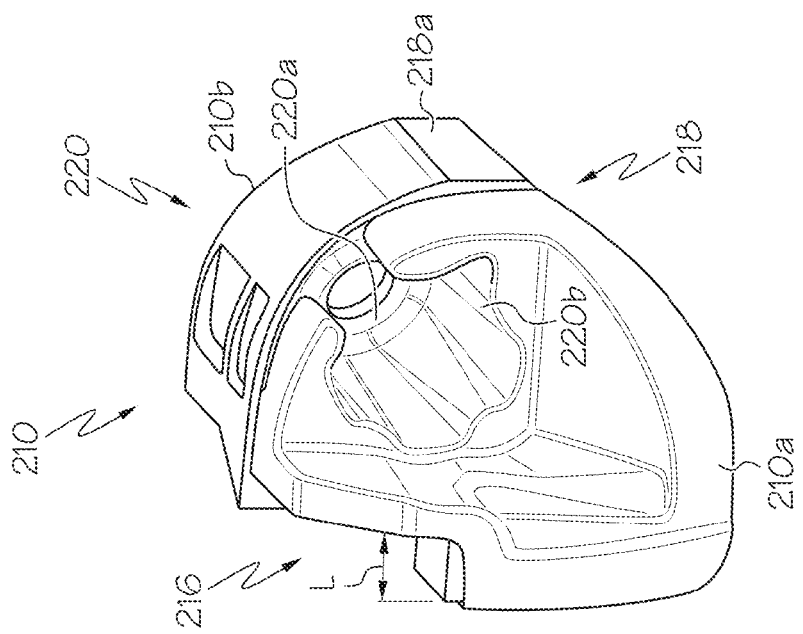
FIG. 12 is a rear perspective view of the exemplary wedge of FIG. 11.
Figure 11:
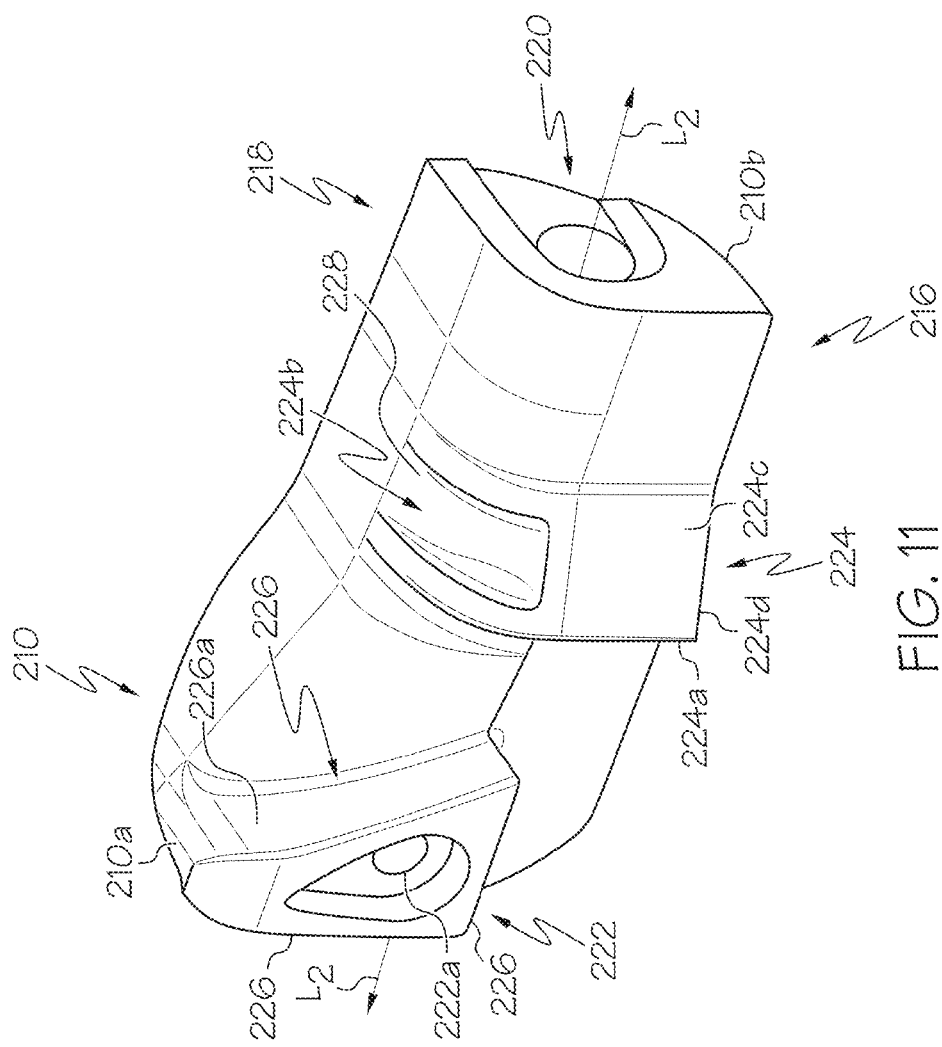
FIG. 11 is a front perspective view of an exemplary wedge of the reservoir retention system of the housing of FIG. 2.

With regard to FIGS. 11 and 12, the wedge 210 can include a first, reservoir facing side 216, a second, housing facing side 218 and a throughbore 220. The first side 216 can be opposite the second side 218. The first side 216 can extend along a longitudinal axis L2 of the wedge 210 for a length that can be substantially greater than a length of the second side 218 along the longitudinal axis L2. The difference in the lengths between the first side 216 and the second side 218 can enable a portion of the reservoir biasing member 212 to be accommodated and guided by a portion of the first side 216 of the wedge 210. The first side 216 can include a first contact portion 222 and a second contact portion 224. With reference to FIG. 11, the first contact portion 222 can be defined at a first end 210a of the wedge 210, and the second contact portion 224 can be defined between the first contact portion 222 and a second end 210b of the wedge 210. It should be noted that the first end 210a of the wedge 210 can contact the first contact surface 148a of the top housing component 108 when the reservoir biasing member 212 is in a second, compressed position, and the second end 210b of the wedge 210 can contact the second contact surface 148b of the top housing component 108 when the reservoir biasing member 212 is in a first, uncompressed position.

The first contact portion 222 can contact or engage a portion of the fluid reservoir 106, and the second contact portion 224 can contact a second portion of the fluid reservoir 106, as will be discussed herein. In one example, the first contact portion 222 can comprise a substantially triangular projection, which can extend outwardly from the first side 216. In one example, the first contact portion 222 can have three sides 226. One of the sides 226 can include a contact face 226a. In one example, the contact face 226a can be formed on the side 226 adjacent to the second contact portion 224. In this example, the contact face 226a can have a slope, which can extend in a direction generally transverse to the longitudinal axis L2. It should be noted, however, that the contact face 226a can have any desired slope, and thus, the slope illustrated herein is merely exemplary. In one example, the slope angle can be less than about 45 degrees to reduce insertion forces associated with the insertion of the fluid reservoir 106. The contact face 226a can contact and guide a portion of the fluid reservoir 106 into the housing 102. The first contact portion 222 can also include a recess 222a, which can facilitate the forming of the wedge 210.

The second contact portion 224 can comprise a projection, which can project outwardly from the first side 216. In one example, the second contact portion 224 can include four sides 224a-224d. The first side 224a can have a length L (FIG. 12), which can define the distance the second contact portion 224 projects or extends outwardly from the first side 216. The length L can be selected to aid in biasing the fluid reservoir 106 in a direction opposite the flow direction of fluid from the fluid reservoir 106. In addition, the length L can determine the amount of reservoir length tolerance variability the wedge 210 can accommodate. The second side 224b can define a channel 228, which can aid in the manufacturing of the wedge 210, through injection molding, for example. The third side 224c can contact the portion of the fluid reservoir 106, and can provide a mechanical advantage to resist high occlusion forces with a relatively small amount of load. The fourth side 224d can be adjacent to a surface 110a of the top housing component 108 when the wedge 210 is coupled to the housing 102.

With reference to FIG. 12, the second side 218 can be positioned adjacent to the second end 126 of the housing 102 when the wedge 210 is coupled to the housing 102. Thus, the wedge 210 can move relative to the second end 126, in a direction substantially parallel to the second end 126, when the wedge 210 is coupled to the housing 102. The second side 218 can include a housing contact surface 218a. The housing contact surface 218a can contact the second end 126 of the housing 102 to restrict the rotation of the wedge 210 relative to the housing 102. In one example, the housing contact surface 218a can comprise a flat surface, which can cooperate with a flat surface formed on the second end 126 to restrict or limit the angular movement of the wedge 210.

With continued reference to FIGS. 11 and 12, the throughbore 220 can be defined between the first side 216 and second side 218 and can extend along the longitudinal axis L2 of the wedge 210 from the first end 210a to the second end 210b. The throughbore 220 can be substantially circumferentially open at and near the first end 210a of the wedge 210 (FIG. 12), and can be substantially circumferentially closed at and near the second end 210b (FIG. 11). The throughbore 220 can slidably receive the retention member 214 to movably couple the wedge 210 to the housing 102, and can also receive a portion of the reservoir biasing member 212. Generally, the retention member 214 can be slidably received through the throughbore 220 from the first end 210a to the second end 210b, and the reservoir biasing member 212 can be coupled to and received within the throughbore 220 at the first end 210a of the wedge 210. In one example, with regard to FIG. 12, the throughbore 220 can include a lip 220a near the second end 210b, which can contact an end of the reservoir biasing member 212. A portion of the throughbore 220 can also have an undulating surface, which can aid in manufacturing the wedge 210.

With reference back to FIG. 4B, the reservoir biasing member 212 can include a first end 212a and a second end 212b. The first end 212a can contact the lip 220a of the throughbore 220, and the second end 212b can contact a face defined around the retaining bore 150a of the top housing component 108. In one example, the reservoir biasing member 212 can comprise a coil spring, however, any suitable biasing mechanism could be employed, including a metal, metal alloy or polymeric biasing mechanism. The reservoir biasing member 212 can provide a spring force F, which can bias the wedge 210 against the side 133 of the top housing component 108 in the first, uncompressed position. In the second, compressed position, the reservoir biasing member 212 can be compressed by the fluid reservoir 106 such that the wedge 210 contacts the second contact surface 148b of the top housing component 108.

The retention member 214 can couple the wedge 210 and the reservoir biasing member 212 to the top housing component 108. In one example, the retention member 214 can comprise a pin, which can have a first end 214a and a second end 214b. The first end 214a and the second end 214b can be fixedly coupled to the first retaining bore 150a and second retaining bore 150b, respectively, of the top housing component 108. In one example, the retention member 214 can be coupled to the top housing component 108 by adhesives, however, the retention member 214 can be coupled to the top housing component 108 via any suitable technique, such as press-fitting, mechanical fasteners, etc. As a further example, the retention member 214 can be coupled to the top housing component 108 through a press-fit and visible light cure adhesive.

With reference to FIG. 4B, the fluid reservoir 106 can be removably coupled to the housing 102. In one example, the fluid reservoir 106 can include a first or barrel portion 230 and a second portion or plunger guide 232. Generally, the barrel portion 230 can be removably coupled to the top housing component 108, while the plunger guide 232 can be removably coupled to the bottom housing component 110. The barrel portion 230 can contain a first end 234, a second end 236 and a reservoir 238 defined between the first end 234 and the second end 236.

With regard to FIG. 13, the first end 234 can cooperate with the reservoir engagement system 114 to couple the fluid reservoir 106 to the housing 102 and bias the fluid reservoir 106 in a direction substantially opposite the direction of fluid flow out of the fluid reservoir 106. In one example, the first end 234 of the barrel portion 230 can include a delivery port 240, a first alignment feature 242, a second alignment feature 244 and a third alignment feature 246. It should be noted that the use of three alignment features is merely exemplary, as the barrel portion 230 could include any number of alignment features to aid in coupling the fluid reservoir 106 to the housing 102.

The delivery port 240 can establish the fluid flow path to the patient. Generally, the fluid can flow from the reservoir 238 out the delivery port 240 into the cannula 107 for delivery to the patient. The delivery port 240 can include a pierceable septum if the fluid reservoir 106 is a prefilled unit. Alternatively, the delivery port 240 may include a vented opening to accommodate filling of the fluid reservoir 106 by the patient, a doctor, a caregiver, or the like. In one example, the delivery port 240 can be formed near or along a first side 234a of the first end 234 and the first alignment feature 242, second alignment feature 244 and third alignment feature 246 can be formed near or along a second side 234b of the first end 234.

The first alignment feature 242 can be substantially opposite the delivery port 240. The first alignment feature 242 can laterally align the fluid reservoir 106 relative to the housing 102. In one example, the first alignment feature 242 can comprise a geometric projection. For example, the first alignment feature 242 can include one or more walls 248. In one example, the walls 248 can cooperate to define a geometric projection having a substantially rectangular shape. In this example, one of the walls 248a can be arcuate, to conform with the surface 108a of the top housing component 108. It should be noted that the geometric shape formed by the walls 248 is merely exemplary, as the first alignment feature 242 can have any desired shape to constrain and align the fluid reservoir 106 relative to the housing 102. Generally, the first alignment feature 242 can be positioned near the first end 210a of the wedge 210 when the fluid reservoir 106 is coupled to the housing 102.

The second alignment feature 244 can be defined between the first alignment feature 242 and the third alignment feature 246. In one example, the second alignment feature 244 can comprise a wall. The second alignment feature 244 can have a first surface 250 and a second surface 252. The first surface 250 can extend outwardly from the first end 234 so as to be substantially perpendicular to a longitudinal axis of the barrel portion 230, while the second surface 252 can be arcuate. The arcuate shape of the second surface 252 can act as a ramp, which can cooperate with the third side 224c of the second contact portion 224 of the wedge 210. The contact between the second surface 252 and the wedge 210 can bias the fluid reservoir 106 in the direction opposite of the direction of fluid flow out of the reservoir 238, as illustrated in FIG. 14. In FIG. 14, the contact between the second surface 252 and the second contact portion 224 of the wedge 210 biases the fluid reservoir 106 relative to the housing 102. In this example, $D_B$ can indicate the direction the fluid reservoir 106 is biased relative to the housing, and $D_F$ can indicate the direction of fluid flow out of the fluid reservoir 106. $D_B$ can be substantially opposite $D_F$. Generally, the fluid reservoir 106 can be biased by the wedge 210 such that the fluid reservoir 106 contacts the at least one contact face 166 of the bottom housing component 110. The second alignment feature 244 can also cooperate with the wedge 210 to provide audible feedback to the user upon coupling the fluid reservoir 106 to the housing 102.

The third alignment feature 246 can comprise a geometric projection, which can extend outwardly from the first end 234. In one example, the third alignment feature 246 can have sides 254, which can include a first side 254a, a second side 254b, a third side 254c and a fourth side 254d. Generally, the third alignment feature 246 can be sized to fit between the first contact portion 222 of the wedge 210 and the surface 108a of the top housing component 108. The second side 254b can be angled relative to the first side 254a and the third side 254c. A contact surface 256 can be formed between the second side 254b and the third side 254c, which can contact and move along the face 226a of the first contact portion 222 of the wedge 210 when the fluid reservoir 106 is coupled to the housing 102. The movement of the contact surface 256 along the first contact portion 222 can cause the wedge 210 to move from a first position to a second position against the force of the reservoir biasing member 212 towards the second side 130 of the top housing component 108. As will be discussed herein, once the contact surface 262 moves past the face 226a of the first contact portion 222, the reservoir biasing member 212 can move from the second, compressed position to the first, uncompressed position, which can move the second contact portion 224 of the wedge 210 into contact with the second alignment feature 244. The movement of the second contact portion 224 into contact with the second alignment feature 244 can cause audible feedback, such as a snap, which can be heard by the user. This can aid the user in determining that the fluid reservoir 106 is properly coupled to the housing 102. The fourth side 254d can be arcuate.

Figure 15:
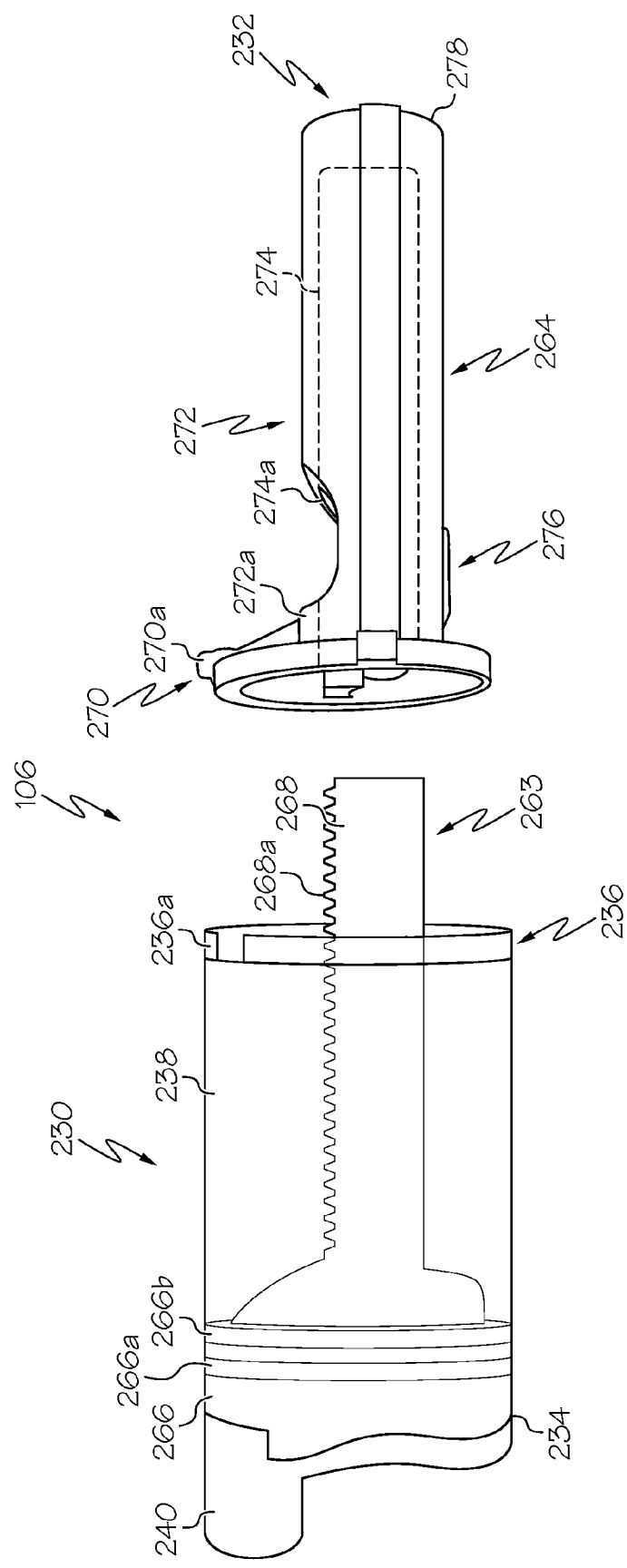
FIG. 15 is a partially exploded view of the exemplary fluid reservoir.

With reference to FIG. 15, the second end 236 of the fluid reservoir 106 can be substantially circumferentially open, and can cooperate with a portion of the plunger guide 232. The second end 236 can also include a slot 236a, which can cooperate with a portion of the plunger guide 232 to couple the plunger guide 232 to the second end 236. The reservoir 238 can be defined between the first end 234 and the second end 236. The reservoir 238 can be prefilled with a fluid, or could be later filled with the fluid, if desired. In this example, the reservoir 238 can receive insulin, but the reservoir 238 can hold any suitable liquid.

The plunger guide 232 can be used to dispense fluid from the reservoir 238. The plunger guide 232 can include a plunger 263 and a housing 264. The plunger 263 can move relative to the housing 264. Generally, the plunger 263 can include a platform 266 and a rack 268 coupled to the platform 266. The platform 266 can include one or more sealing elements 266a, 266b, which can be circumferentially disposed about a perimeter of the platform 266. The sealing elements 266a, 266b can prevent fluid from escaping from the second end 236 of the reservoir 238 when the plunger guide 232 is coupled to the second end 236.

The rack 268 can be fixedly coupled to the platform 266 so that the advancement of the rack 268 can move the platform 266 within the reservoir 238. The rack 268 can include a plurality of teeth 268a, which can meshingly engage a plurality of teeth on a pinion coupled to the housing 102. The rack 268 can be driven by the pinion to advance the platform 266 within the reservoir 238 to dispense fluid out of the delivery port 240.

The housing 264 can include a base 270 and a rack receiving portion 272. The base 270 can be sized and configured to be received within and coupled to the second end 236 of the barrel portion 230. Generally, the base 270 can be substantially oval in shape, and can include a projection 270a. The projection 270a can be received within the slot 236a of the second end 236 of the barrel portion 230 to couple the housing 264 to the barrel portion 230. The cooperation between the projection 270a and slot 236a can provide error-proofing in the assembly of the housing 264 to the barrel portion 230. The base 270 can also define an opening, which can slidably receive a portion of the rack 268 therethrough. The opening of the base 270 can be in communication with the rack receiving portion 272.

The rack receiving portion 272 can extend outwardly from the base 270. The rack receiving portion 272 can include a bore or cavity 274, at least one contact surface 276 and a removal portion 278. In one example, the cavity 274 can be sized to movably or slidably receive the rack 268, and can be in communication with the opening of the base 270. The cavity 274 can also include a cutout portion 274a defined near a first end 272a of the rack receiving portion 272, which can enable the rack 268 to engage the pinion.

Figure 16:
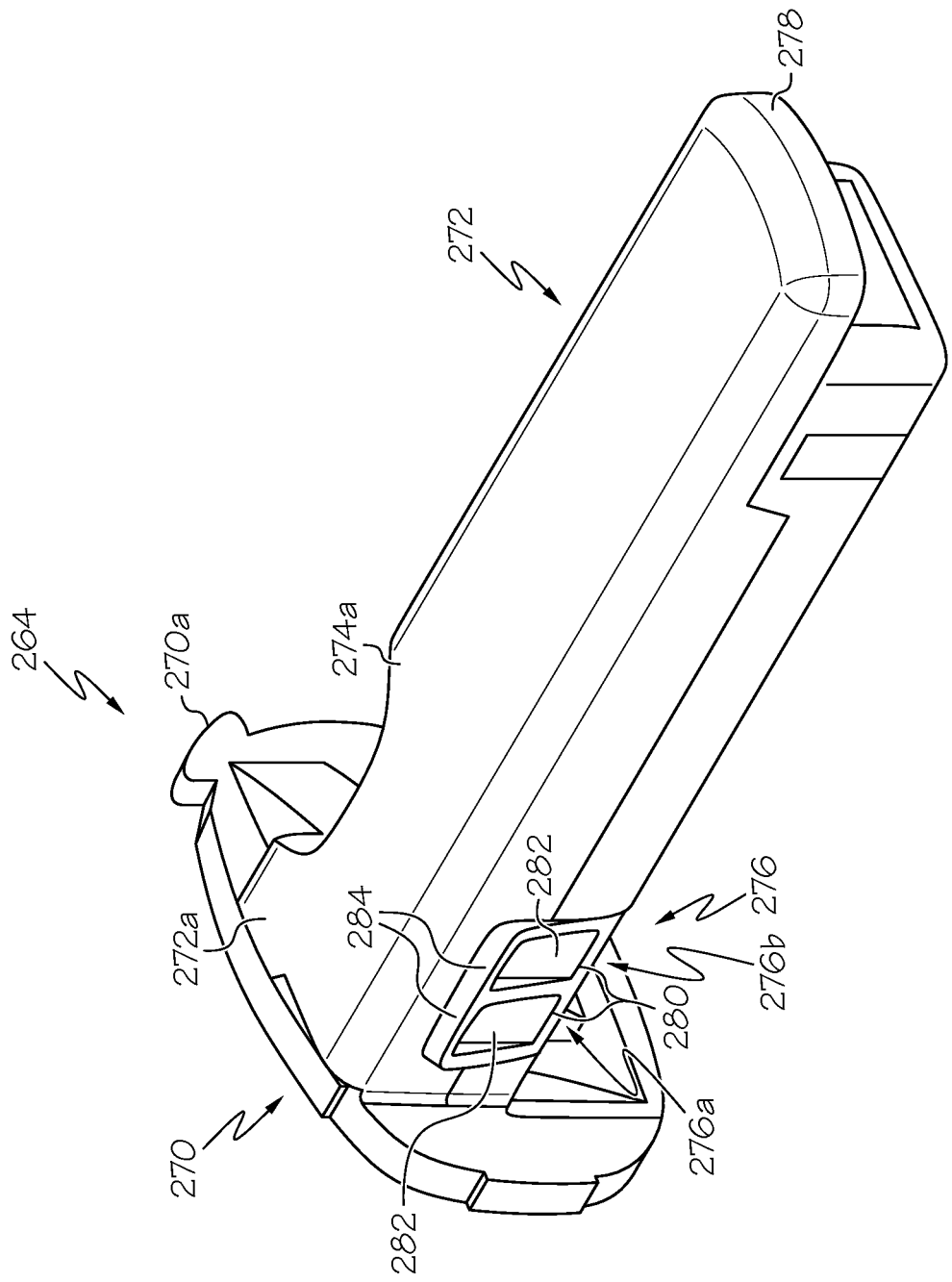
FIG. 16 is a perspective view of an exemplary plunger guide of the fluid reservoir of FIG. 15.

With reference to FIG. 16, the at least one contact surface 276 can be defined near the first end 272a of the rack receiving portion 272. In one example, the at least one contact surface 276 can comprise a first contact surface 276a and a second contact surface 276b. The first contact surface 276a and the second contact surface 276b can cooperate with the pinion engagement system 112 to bias the rack 268 against the pinion and to create an audible feedback upon the proper insertion of the fluid reservoir 106 within the housing 102.

Figure 17:
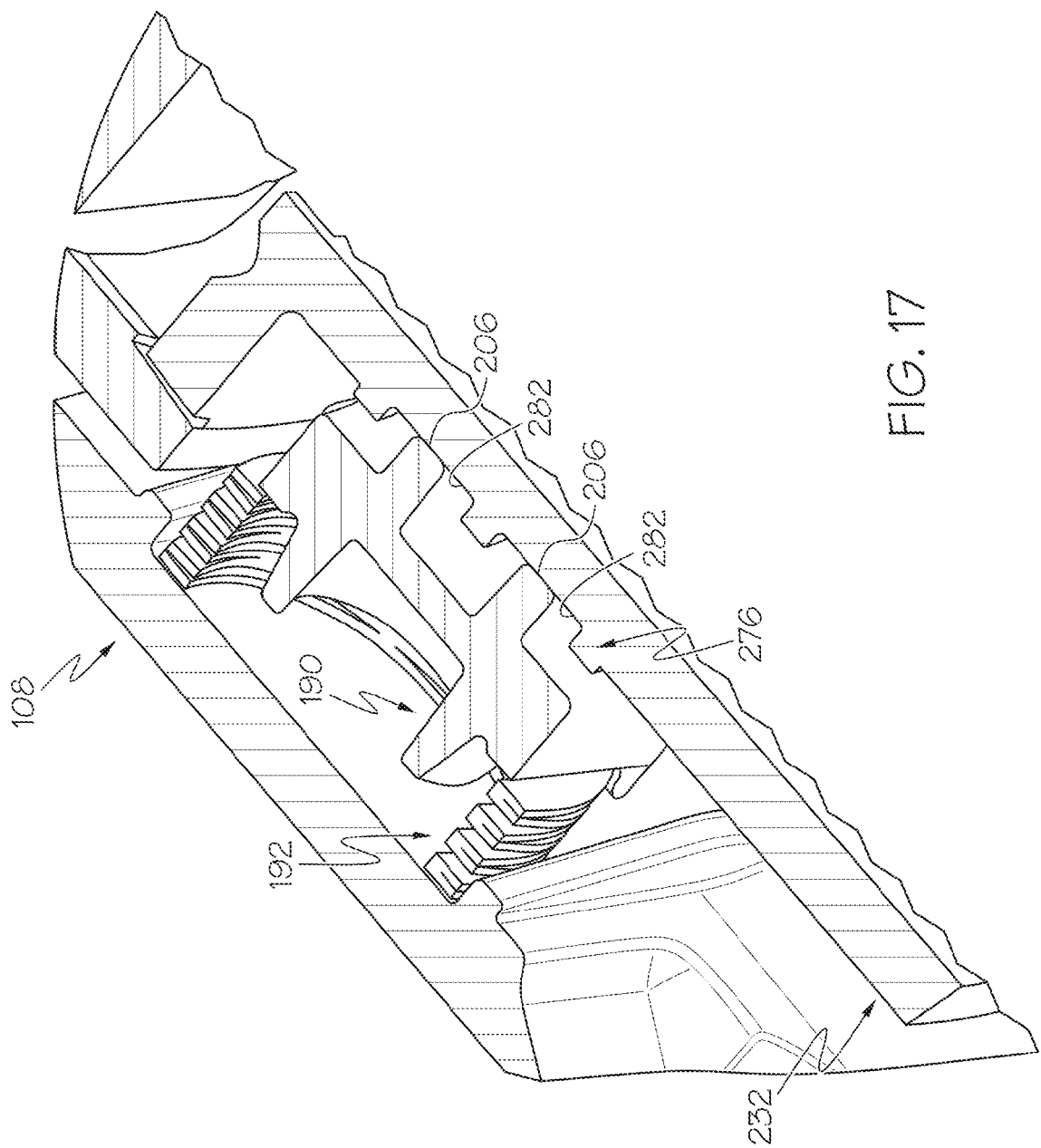
FIG. 17 is a cross-sectional view of the housing of FIG. 2, taken along line 17-17 of FIG. 2, illustrating an exemplary engagement between the plunger guide of the fluid reservoir and the pinion engagement system of the housing of FIG. 2.

In this regard, the first contact surface 276a and the second contact surface 276b can each include an insertion ramp 280, a recess 282 and a removal ramp 284, which can be unitarily formed. It should be noted that although the at least one contact surface 276 is described and illustrated herein as having two contact surfaces, the at least one contact surface 276 could have any number of contact surfaces, including, but not limited to a signal contact surface. The recess 282 can be defined between the insertion ramp 280 and the removal ramp 284, and can receive the contact faces 206 of the snap housing 190 when the fluid reservoir 106 is coupled to the housing 102. The insertion ramp 280 can have a slope, such that as the fluid reservoir 106 is inserted into the housing 102, the insertion ramp 280 can move the snap housing 190 against the force of the biasing member 192. Once the fluid reservoir 106 is properly coupled to the housing 102, the spring force from the biasing member 192 can move or push the snap housing 190 such that contact faces 206 contact the recess 282, as shown in FIG. 17. The contact between the contact faces 206 and the recess 282 can provide audible feedback to the user that the fluid reservoir 106 is coupled to the housing 102.

With reference back to FIG. 16, the removal ramp 284 can aid in the removal of the fluid reservoir 106 from the housing 102. Generally, when the fluid reservoir 106 is coupled to the housing 102, the lip 200 of the snap housing 190 can be disposed over the removal ramp 284. Thus, the removal ramp 284 can have a slope, which can cooperate with the lip 200 of the snap housing 190 to compress the biasing member 192 and move the snap housing 190 to enable the removal of the fluid reservoir 106.

The removal portion 278 can be defined at a second end 272b of the rack receiving portion 272. In one example, the removal portion 278 can comprise a tab, which can be received within a slot 286 defined within the top housing component 108 (FIG. 4B). In this example, the user can lift upwardly on the removal portion 278 to remove the fluid reservoir 106 from the housing 102.

Figure 18B:
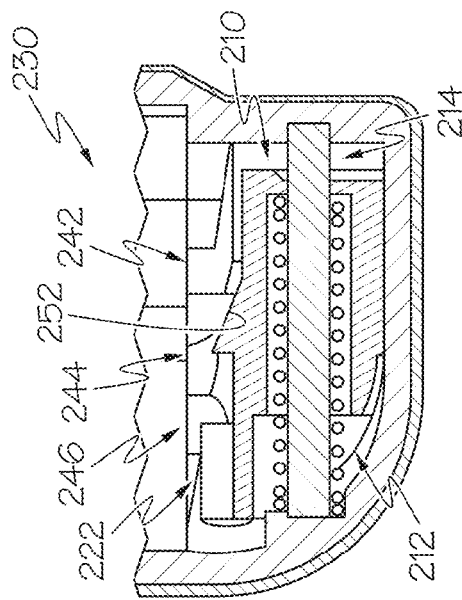
FIG. 18B is a schematic cross-sectional view of the housing of FIG. 2, taken along line 18B-18B of FIG. 18, illustrating an exemplary partial engagement between the barrel portion of the fluid reservoir and the exemplary wedge of the reservoir retention system of the housing of FIG. 2.
Figure 18:
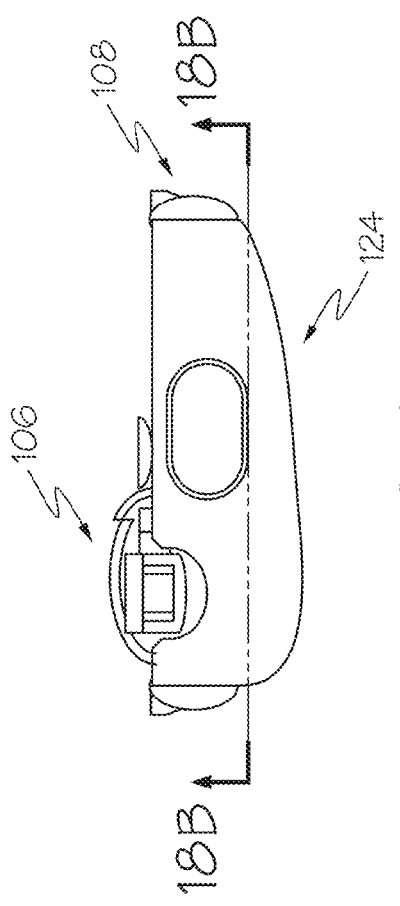
FIG. 18 is an end view of the housing of FIG. 2, with the fluid reservoir partially exploded above the housing.
Figure 18A:
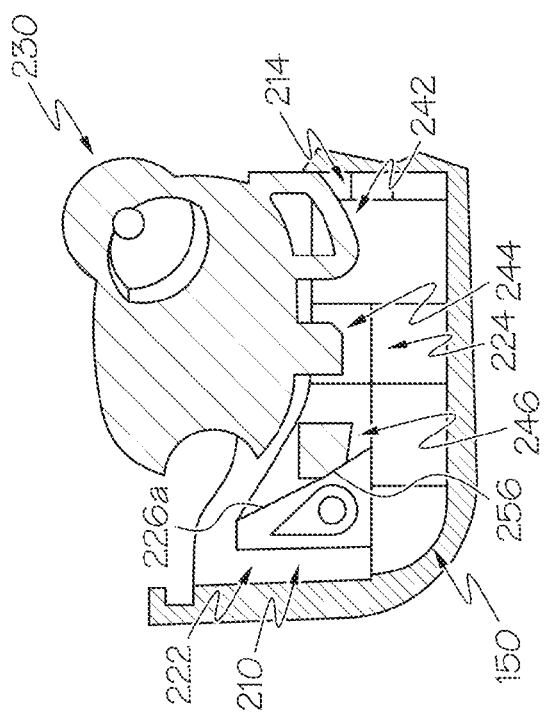
FIG. 18A is a schematic cross-sectional view of the housing of FIG. 18, taken along line 18A-18A of FIG. 2, illustrating an exemplary partial engagement between the barrel portion of the fluid reservoir and the exemplary wedge of the reservoir retention system of the housing of FIG. 2.

In order to assemble the fluid infusion device 100, the bottom housing component 110 can be coupled to the top housing component 108. Then, in one example, the fluid reservoir 106 can be coupled to the housing 102 in a straight in insertion. In this example, the patient can press down on the barrel portion 230 to couple the fluid reservoir 106 to the housing 102. The application of force on the barrel portion 230 can cause the third alignment feature 246 to contact the face 226a of the first contact portion 222 of the wedge 210 (FIG. 18A), which can bias the wedge 210 against the force of the reservoir biasing member 212 (FIG. 18B). The continued application of force on the barrel portion 230 can cause the third alignment feature 246 to slide off the face 226a of the first contact portion 222 (FIG. 19A). This can cause the reservoir biasing member 212 to move from the second, compressed position to the first, uncompressed position (FIG. 19B). The movement of the reservoir biasing member 212 from the second position to the first position can move the wedge 210 such that the second contact portion 224 is in contact with the second alignment feature 244 (FIG. 14). This contact can provide at least an audible feedback that the fluid reservoir 106 is coupled to the housing 102. In addition, the contact between the second contact portion 224 and the second alignment feature 244 can bias the fluid reservoir 106 opposite the direction of fluid flow out of the fluid reservoir 106 (FIGS. 20A and 20B).

Figure 21:
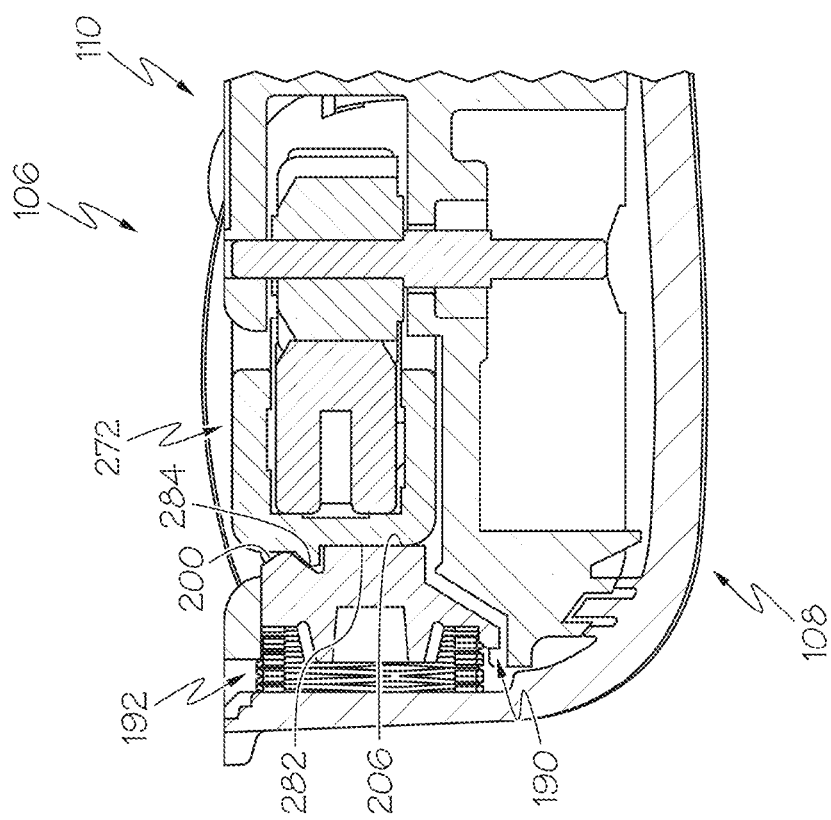
FIG. 21 is a schematic cross-sectional view of the housing of FIG. 2, taken along line 21-21 of FIG. 2, illustrating an exemplary partial engagement between the plunger guide of the fluid reservoir and the pinion engagement system of the housing of FIG. 2.
Figure 22:
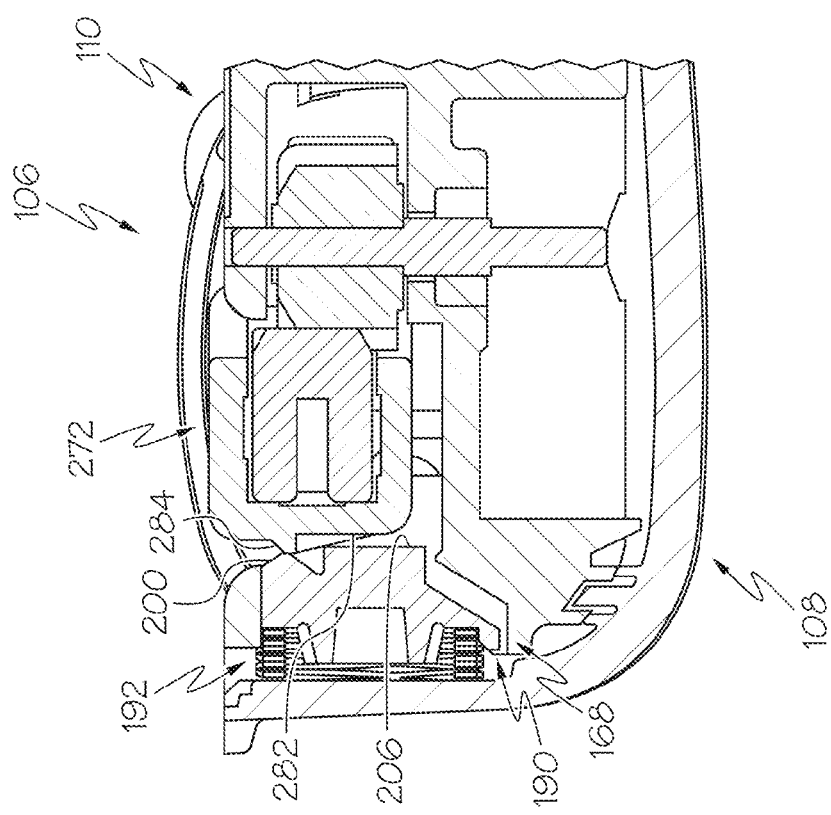
FIG. 22 is a cross-sectional view of the housing of FIG. 2, taken along line 21-21 of FIG. 2, illustrating an exemplary engagement between the plunger guide of the fluid reservoir and the pinion engagement system of the housing of FIG. 2.

Substantially simultaneously, as the third alignment feature 246 slides off the face 226a of the first contact portion 222, the continued application of the force to the barrel portion 230 can cause the insertion ramp 280 of the first contact surface 276a and second contact surface 276b to bias the snap housing 190 against the biasing member 192 (FIG. 21). Then, the contact faces 206 can snap into the recesses 282 of the first contact surface 276a and second contact surface 276b to provide additional audible feedback that the fluid reservoir 106 is coupled to the housing 102 (FIG. 22).

In another example, the fluid reservoir 106 can be inserted into the housing 102 similar to the insertion of a battery into a battery housing. In this example, the barrel portion 230 can be inserted at an angle into the second compartment 120 of the top housing component 108, and generally rotated slightly so that the second surface 252 can contact the second contact portion 224 of the wedge 210. This contact can bias the wedge 210 against the force of the reservoir biasing member 212.

Then, the plunger guide 232 can be inserted into the reservoir receiving portion 170 of the bottom housing portion 110. The application of force to the plunger guide 232 can cause the insertion ramp 280 of the first contact surface 276a and second contact surface 276b to bias the snap housing 190 against the biasing member 192. Then, the contact faces 206 can snap into the recesses 282 of the first contact surface 276a and second contact surface 276b to provide additional audible feedback that the fluid reservoir 106 is coupled to the housing 102.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid reservoir for use with a fluid infusion device, comprising:
 a first portion having a first end and a second end, the first end including an alignment feature and a delivery port;
 a second portion including a housing coupled to the second end of the first portion and a plunger having a rack, with the plunger movable within the housing and the first portion to advance a fluid out of the delivery port, the rack contained wholly within the first portion and the second portion;
 a reservoir defined between the first portion and the second portion that receives the fluid;
 wherein the rack cooperates with a pinion to advance the plunger within the first portion; wherein the housing further comprises: a base that is couplable to the second end of the first portion; and a rack receiving portion including a contact surface adjacent to the base and a removal portion, wherein the base defines an opening and the rack receiving portion defines a bore in communication with the opening to slidably receive the rack, the bore including a cutout portion to enable the rack to engage the pinion.

2. The fluid reservoir of claim 1, wherein the alignment feature further comprises a first alignment feature substantially opposite the delivery port.

3. The fluid reservoir of claim 2, wherein the first alignment feature is a substantially rectangular projection for constraining movement of the fluid reservoir.

4. The fluid reservoir of claim 2, wherein the alignment feature further comprises a second alignment feature, which includes a ramp surface.

5. The fluid reservoir of claim 4, wherein the alignment feature further comprises a third alignment feature, and the second alignment feature is formed between the first alignment feature and the second alignment feature.

6. The fluid reservoir of claim 5, wherein the third alignment feature is a geometric projection.

7. The fluid reservoir of claim 1, wherein the contact surface further comprises a first contact surface and a second contact surface, which each include at least one ramp.

8. The fluid reservoir of claim 7, wherein the first contact surface and the second contact surface each include a first ramp spaced apart from a second ramp by a recess.

9. The fluid reservoir of claim 1, wherein the rack receiving portion is coupled to the base at a first end, and the removal portion is defined at a second end of the rack receiving portion, opposite the first end.

10. The fluid reservoir of claim 1, wherein the fluid is insulin.

11. A fluid reservoir for use with a fluid infusion device, comprising:
- a first portion having a first end and a second end, the first end including a first alignment feature spaced apart from a second alignment feature and a delivery port adjacent to the first alignment feature;
- a second portion including a plunger having a rack and a housing, at least a portion of the plunger received in the housing and movable within the first portion and the housing to advance a fluid out of the delivery port and the housing coupled to the second end of the first portion and the rack contained wholly within the first portion and the second portion;
- a reservoir defined between the first portion and the second portion that receives the fluid;
- wherein the rack cooperates with a pinion to advance the plunger within the first portion;
- wherein the housing further comprises: a base that is couplable to the second end of the first portion; and a rack receiving portion including a contact surface and a removal portion, wherein the base defines an opening and the rack receiving portion defines a bore in communication with the opening to slidably receive the rack, the bore including a cutout portion to enable the rack to engage the pinion.

12. The fluid reservoir of claim 11, wherein the first end of the first portion further comprises a third alignment feature, the second alignment feature positioned between the first alignment feature and the third alignment feature, the third alignment feature including a geometric projection.

13. The fluid reservoir of claim 12, wherein the first alignment feature is substantially opposite the delivery port at the first end.

14. The fluid reservoir of claim 11, wherein the first alignment feature is a substantially rectangular projection for constraining movement of the fluid reservoir.

15. The fluid reservoir of claim 11, wherein the second alignment feature includes a ramp surface.

* * * * *